US009658196B2

(12) United States Patent
Chou et al.

(10) Patent No.: US 9,658,196 B2
(45) Date of Patent: *May 23, 2017

(54) GAS COLLECTION AND ANALYSIS SYSTEM WITH FRONT-END AND BACK-END PRE-CONCENTRATORS AND MOISTURE REMOVAL

(71) Applicant: TricornTech Corporation, San Jose, CA (US)

(72) Inventors: Tsung-Kuan A. Chou, San Jose, CA (US); Li-Peng Wang, Taipei (TW); Chia-Jung Lu, Zhongli (TW); Shih-Chi Chu, Taipei (TW)

(73) Assignee: TricornTech Corporation, San Jose, CA (US)

( * ) Notice: Subject to any disclaimer, the term of this patent is extended or adjusted under 35 U.S.C. 154(b) by 167 days.

This patent is subject to a terminal disclaimer.

(21) Appl. No.: 14/248,084

(22) Filed: Apr. 8, 2014

(65) Prior Publication Data

US 2014/0216134 A1    Aug. 7, 2014

Related U.S. Application Data

(63) Continuation of application No. 12/847,593, filed on Jul. 30, 2010, now Pat. No. 8,707,760.
(Continued)

(51) Int. Cl.
*G01N 30/02* (2006.01)
*G01N 30/06* (2006.01)
(Continued)

(52) U.S. Cl.
CPC .......... *G01N 30/06* (2013.01); *B01D 53/261* (2013.01); *G01N 30/02* (2013.01); *G01N 30/08* (2013.01);
(Continued)

(58) Field of Classification Search
CPC ......... G01N 30/465; G01N 2030/8881; G01N 30/466; G01N 30/468; G01N 2030/085;
(Continued)

(56) References Cited

U.S. PATENT DOCUMENTS 3,112,639 A    12/1963   Maxwell
3,538,744 A    11/1970   Karasek
(Continued)

FOREIGN PATENT DOCUMENTS

CN    2192933    3/1995
CN    2439025    7/2001
(Continued)

OTHER PUBLICATIONS

Phillips, M. et. al., "Prediction of Lung Cancer using Volatile Biomarkers in Breath," Cancer Biomarkers, 3, (2007), p. 95-109.
(Continued)

*Primary Examiner* — Lisa Caputo
*Assistant Examiner* — Punam Roy
(74) *Attorney, Agent, or Firm* — Blakely Sokoloff Taylor & Zafman

(57) ABSTRACT

Embodiments of an apparatus including a front-end pre-concentrator module including an inlet, an outlet, and at least one valve to control flow through the inlet, the outlet, or both. The apparatus includes a back-end pre-concentrator module including an inlet, an outlet, and at least one valve to control flow through the inlet, the outlet, or both, and also includes a gas analysis module having an inlet and an outlet and including a gas chromatograph having an inlet and an outlet. The outlet of the front-end pre-concentrator and the outlet of the back-end pre-concentrator are coupled to the inlet of the gas analysis module. Other embodiments are also disclosed and claimed.

33 Claims, 15 Drawing Sheets

Related U.S. Application Data

(60) Provisional application No. 61/326,433, filed on Apr. 21, 2010, provisional application No. 61/230,647, filed on Jul. 31, 2009.

(51) Int. Cl.
| | | |
|---|---|---|
| *B01D 53/26* | (2006.01) | |
| *G01N 30/88* | (2006.01) | |
| *G01N 30/38* | (2006.01) | |
| *G01N 1/22* | (2006.01) | |
| *G01N 1/40* | (2006.01) | |
| *G01N 35/00* | (2006.01) | |
| *G01N 30/00* | (2006.01) | |
| *G01N 30/08* | (2006.01) | |
| *G01N 30/12* | (2006.01) | |
| *G01N 30/60* | (2006.01) | |

(52) U.S. Cl.
CPC .......... *G01N 30/38* (2013.01); *G01N 30/88* (2013.01); *B01D 2251/302* (2013.01); *B01D 2251/304* (2013.01); *B01D 2257/91* (2013.01); *G01N 1/2205* (2013.01); *G01N 1/4077* (2013.01); *G01N 30/12* (2013.01); *G01N 30/6095* (2013.01); *G01N 35/00871* (2013.01); *G01N 2001/2276* (2013.01); *G01N 2030/0095* (2013.01); *G01N 2030/085* (2013.01)

(58) Field of Classification Search
CPC ..... G01N 2030/201; G01N 2030/3061; G01N 30/88; G01N 2030/628; G01N 35/1097
See application file for complete search history.

(56) References Cited

U.S. PATENT DOCUMENTS

| | | | |
|---|---|---|---|
| 4,470,298 A | 9/1984 | Jibelian | |
| 4,670,405 A | 6/1987 | Stetter et al. | |
| 4,869,876 A | 9/1989 | Arfman et al. | |
| 4,873,058 A | 10/1989 | Arnold et al. | |
| 4,888,295 A | 12/1989 | Zaromb et al. | |
| 4,948,389 A | 8/1990 | Klein et al. | |
| 5,071,547 A * | 12/1991 | Cazer ................. | B01D 15/1864 210/198.2 |
| 5,092,155 A | 3/1992 | Rounbehler et al. | |
| 5,108,468 A | 4/1992 | Ligon, Jr. | |
| 5,108,705 A | 4/1992 | Rounbehler et al. | |
| 5,109,691 A | 5/1992 | Corrigan et al. | |
| 5,152,176 A | 10/1992 | Bryselbout et al. | |
| 5,268,302 A | 12/1993 | Rounbehler et al. | |
| 5,281,256 A | 1/1994 | Sacks et al. | |
| 5,352,585 A * | 10/1994 | Binder ................. | G01N 30/461 422/70 |
| 5,376,252 A | 12/1994 | Ekstrom et al. | |
| 5,416,023 A * | 5/1995 | Binder ................. | G01N 30/461 210/198.2 |
| 5,471,055 A | 11/1995 | Costanzo et al. | |
| 5,492,555 A | 2/1996 | Strunk et al. | |
| 5,611,846 A | 3/1997 | Overton et al. | |
| 5,770,088 A | 6/1998 | Ikeda et al. | |
| 5,979,221 A | 11/1999 | Walte et al. | |
| 5,983,703 A | 11/1999 | Wylie et al. | |
| 5,983,710 A | 11/1999 | Uhen et al. | |
| 6,165,251 A * | 12/2000 | Lemieux ................. | B01D 53/04 95/82 |
| 6,258,263 B1 | 7/2001 | Henderson et al. | |
| 6,306,200 B1 | 10/2001 | Yu | |
| 6,497,138 B1 | 12/2002 | Abdel-Rahman et al. | |
| 6,527,835 B1 * | 3/2003 | Manginell ............ | G01F 1/6845 55/524 |
| 6,759,013 B2 | 7/2004 | Kaltenbach et al. | |
| 6,792,794 B2 | 9/2004 | Bonne et al. | |
| 6,828,910 B2 | 12/2004 | VanRyzin et al. | |
| 6,914,220 B2 | 7/2005 | Tian et al. | |
| 7,153,272 B2 | 12/2006 | Talton | |
| 7,223,970 B2 | 5/2007 | Miller et al. | |
| 7,273,517 B1 | 9/2007 | Lewis et al. | |
| 7,343,779 B1 | 3/2008 | Yu | |
| 7,437,779 B2 | 10/2008 | Kenny et al. | |
| 7,530,259 B2 | 5/2009 | Tai et al. | |
| 7,608,818 B2 | 10/2009 | Miller et al. | |
| 7,926,368 B2 | 4/2011 | Ryan | |
| 8,087,283 B2 | 1/2012 | Wang et al. | |
| 8,104,513 B2 | 1/2012 | Furukawa | |
| 8,277,544 B2 | 10/2012 | Guan et al. | |
| 8,613,215 B2 | 12/2013 | Lambertus et al. | |
| 8,707,760 B2 * | 4/2014 | Chou .................. | B01D 53/261 73/23.3 |
| 8,978,444 B2 * | 3/2015 | Chou .................. | G01N 29/022 73/23.42 |
| 2001/0039880 A1 | 11/2001 | Gellert et al. | |
| 2002/0148353 A1 | 10/2002 | Seeley | |
| 2003/0015019 A1 | 1/2003 | O'Brien | |
| 2003/0233862 A1 | 12/2003 | Wise et al. | |
| 2004/0236244 A1 | 11/2004 | Allen et al. | |
| 2005/0063865 A1 | 3/2005 | Bonne et al. | |
| 2005/0065446 A1 | 3/2005 | Talton | |
| 2005/0085740 A1 | 4/2005 | Davis et al. | |
| 2005/0199121 A1 | 9/2005 | Crnko et al. | |
| 2005/0223775 A1 | 10/2005 | Klee et al. | |
| 2005/0264926 A1 | 12/2005 | Burts-Cooper et al. | |
| 2005/0274174 A1 | 12/2005 | Tai et al. | |
| 2005/0277200 A1 | 12/2005 | Cai et al. | |
| 2006/0038402 A1 | 2/2006 | Norman et al. | |
| 2006/0046749 A1 | 3/2006 | Pomerantz et al. | |
| 2006/0144237 A1 | 7/2006 | Liang et al. | |
| 2006/0196249 A1 | 9/2006 | Syage et al. | |
| 2006/0222568 A1 | 10/2006 | Wang et al. | |
| 2007/0000305 A1 | 1/2007 | Ma et al. | |
| 2007/0000838 A1 | 1/2007 | Shih et al. | |
| 2007/0029477 A1 | 2/2007 | Miller et al. | |
| 2007/0062255 A1 | 3/2007 | Talton | |
| 2007/0193336 A1 | 8/2007 | McCurry et al. | |
| 2007/0256474 A1 | 11/2007 | Paakkanen et al. | |
| 2008/0092626 A1 | 4/2008 | Lehmann | |
| 2008/0121016 A1 | 5/2008 | Shah et al. | |
| 2008/0121017 A1 | 5/2008 | Shah et al. | |
| 2008/0233636 A1 | 9/2008 | Ryan | |
| 2008/0264491 A1 | 10/2008 | Klee et al. | |
| 2008/0300501 A1 | 12/2008 | Willard et al. | |
| 2009/0126457 A1 | 5/2009 | Fisher | |
| 2009/0238722 A1 | 9/2009 | Mora-Fillat et al. | |
| 2009/0321356 A1 * | 12/2009 | Gerhardt ............ | G01N 30/6095 210/656 |
| 2010/0000291 A1 | 1/2010 | White | |
| 2011/0005300 A1 | 1/2011 | Wang et al. | |
| 2011/0023581 A1 | 2/2011 | Chou et al. | |
| 2011/0113866 A1 | 5/2011 | Finlay | |
| 2011/0143952 A1 | 6/2011 | Lewis et al. | |
| 2011/0252873 A1 | 10/2011 | Vorm | |
| 2011/0259081 A1 | 10/2011 | Chou et al. | |
| 2012/0090378 A1 | 4/2012 | Wang et al. | |
| 2014/0216134 A1 | 8/2014 | Chou et al. | |
| 2014/0298990 A1 * | 10/2014 | Fan ...................... | G01N 30/463 95/23 |

FOREIGN PATENT DOCUMENTS

| | | |
|---|---|---|
| CN | 2520508 Y | 11/2002 |
| CN | 1584589 A | 2/2005 |
| CN | 1615430 A | 5/2005 |
| CN | 2798088 Y | 7/2006 |
| CN | 2859526 | 1/2007 |
| CN | 1301406 C | 2/2007 |
| CN | 1910453 A | 2/2007 |
| CN | 1954208 A | 4/2007 |
| CN | 1979172 A | 6/2007 |
| CN | 100391403 C | 6/2008 |
| CN | 101196457 A | 6/2008 |
| CN | 101263385 A | 9/2008 |
| CN | 201133905 Y | 10/2008 |

(56) References Cited

FOREIGN PATENT DOCUMENTS

| | | |
|---|---|---|
| CN | 100454019 A | 1/2009 |
| CN | 101611304 A | 12/2009 |
| CN | 101641596 A | 2/2010 |
| DE | 196 01 571 A1 | 7/1997 |
| EP | 0 573 060 A2 | 12/1993 |
| EP | 0 574 027 A2 | 12/1993 |
| EP | 0 654 667 A1 | 5/1995 |
| EP | 2 045 593 A2 | 4/2009 |
| EP | 2 065 703 A1 | 6/2009 |
| EP | 2 065 704 A1 | 6/2009 |
| GB | 874 742 A | 8/1961 |
| JP | 60-230058 | 11/1985 |
| JP | 6-242095 | 9/1994 |
| JP | 07-209272 A | 8/1995 |
| JP | 7-318545 A | 12/1995 |
| JP | 2001-194373 A | 7/2001 |
| JP | 2003057223 A | 2/2003 |
| JP | 2006501448 A | 1/2009 |
| JP | 2011-514674 | 6/2009 |
| JP | 2009-183905 A | 8/2009 |
| TW | 555951 B | 10/2003 |
| TW | 201000070 A | 1/2010 |
| WO | WO 01/55714 A1 | 8/2001 |
| WO | WO 03/064994 A2 | 8/2003 |
| WO | WO 2005-071395 A1 | 8/2005 |
| WO | WO 2005/111599 A1 | 11/2005 |
| WO | WO 2006/113527 A2 | 10/2006 |
| WO | WO 2007/010425 A1 | 1/2007 |
| WO | WO 2008/094030 A1 | 8/2008 |
| WO | WO 2009-057256 A1 | 5/2009 |
| WO | WO 2009/069000 A2 | 6/2009 |

OTHER PUBLICATIONS

Phillips, M. et. al., "Volatile Biomarkers of Pulmonary Tuberculosis in the Breath," Tuberculosis, (2007) 87, p. 44-52.
Hanson III, C.W. et al., "Electronic Nose Prediction of a Clinical Pneumonia Score: Biosensors and Microbes," Anesthesiology, vol. 102, No. 1, p. 63-68, Jan. 2005.
Dutta, R. et. al., "Bacteria Classification using Cyranose 320 Electronic Nose," BioMedical Engineering OnLine 2002, Published Oct. 16, 2002, pp. 1-7.
Bae, B. et. al., "A Fully-Integrated MEMS Preconcentrator for Rapid Gas Sampling," The 14th International Conference on Solid-State Sensors, Actuators and Microsystems, Lyon, France, Jun. 10-14, 2007 Transducers 2007 International Volume, Issue, p. 1497-1500.
Lambertus, G. et. al., "Design, Fabrication, and Evaluation of Microfabricated Columns for Gas Chromatography," Analytical Chemistry, vol. 76, No. 9, May 1, 2004, p. 2629-2637.
Rowe, M.P. et. al., "Exploiting Charge-Transfer Complexation for Selective Measurement of Gas-Phase Olefins with Nanoparticle-Coated Chemiresistors," Analytical Chemistry, vol. 79, No. 3 Feb. 1, 2007, p. 1164-1172.
Wohltjen, H. et al., "Colloidal Metal—Insulator—Metal Ensemble Chemiresistor Sensor," Analytical Chemistry, vol. 70, No. 14, Jul. 15, 1998, pp. 2856-2859.
Lambertus, G. et al., "Stop-Flow Programmable Selectivity with a Dual-Column Ensemble of Microfabricated Etched Silicon Columns and Air as Carrier Gas," Analytical Chemistry, vol. 77, No. 7, Apr. 1, 2005, pp. 2078-2084.
Tian, W. et al., "Multiple-Stage Microfabricated Preconcentrator-Focuser for Micro Gas Chromatography System," Journal of Microelectromechanical Systems, vol. 14, No. 3, Jun. 2005, pp. 498-507.
de Alencastro, L. F. et al., "Application of Multidimensional (Heart-Cut) Gas Chromatography to the Analysis of Complex Mixtures of Organic Pollutants in Environmental Samples," Environmental Analysis, Chimia 57, No. 9, (2003) pp. 499-504.
Mark Libardoni a,*, P.T. Stevens a, J. Hunter Waite b, Richard Sacks, "Analysis of human breath samples with a multi-bed sorption trap and comprehensive two-dimensional gas chromatography (GC×GC)," Journal of Chromatography B, 842, pp. 13-21, 2006.
Phillips, M. et al., "Breath biomarkers of active pulmonary tuberculosis," Elsevier, Diagnostics, Tuberculosis (2010) pp. 1-7.
PCT/US2009/045872, PCT International Search Report and Written Opinion, mail date Jul. 27, 2009, 11 pages.
PCT/US2010/041243, PCT International Search Report and Written Opinion, mail date Feb. 17, 2011, 7 pages.
PCT/US2010/044165, PCT International Search Report and Written Opinion, mail date Apr. 29, 2011, 8 pages.
U.S. Office Action mailed Dec. 22, 2010, U.S. Appl. No. 12/140,822, filed Jun. 17, 2008, 16 pages.
U.S. Office Action mailed May 18, 2011, U.S. App. No. 12/140,822, filed Jun. 17, 2008, 6 pages.
U.S. Notice of Allowance mailed Aug. 30, 2011, U.S. Appl. No. 12/140,822, filed Jun. 17, 2008, 9 pages.
EP Application No. 09767436.0, Supplementary European Search Report and the European Search Opinion, Dec. 22, 2011, 8 pages.
PCT/US2011/033325, PCT International Search Report and Written Opinion, mail date Jan. 6, 2012, 7 pages.
Manolis, A., "The Diagnostic Potential of Breath Analysis," Clinical Chemistry 29, No. 1, pp. 5-15, (1983).
Ho, C. K. et al., "Review of Chemical Sensors for In-Situ Monitoring of Volatile Contaminants," Sandia Report, SAND2001-0643, pp. 1-28, (2001).
Riegel, J. et al., "Exhaust gas sensors for automotive emission control," Elsevier, Solid State Ionics 152-153, pp. 783-800, (2002).
Eranna, G. et al., "Oxide Materials for Development of Integrated Gas Sensors—A Comprehensive Review," Critical Reviews in Solid State and Materials Sciences, 29, pp. 111-188, (2004).
Arshak, K. et al., "A review of gas sensors employed in electronic nose applications," Sensor Review, vol. 24, No. 2, pp. 181-198, (2004).
Yamazoe, N., "Toward innovations of gas sensor technology," Elsevier, Sensors and Actuators B, No. 108, pp. 2-14, (2005).
Cao, W. et al., "Breath Analysis: Potential for Clinical Diagnosis and Exposure Assessment," Clinical Chemistry, 52, No. 5, pp. 800-811, (2006).
Buszewski, B. et al., "Human exhaled air analytics: biomarkers of diseases" Review, Biomedical Chromatography, 21, pp. 553-566, (2007).
Ohira, S.-I. et al., "Micro gas analyzers for environmental and medical applications," Elsevier, Science Direct, Analytica Chimica Acta 619, pp. 143-156, (2008).
Peng, G. et al., "Diagnosing lung cancer in exhaled breath using gold nanoparticles," Nature Nanotechnology, vol. 4, pp. 669-673, (2009).
Barnes, P. J. et al., "Exhaled Nitric Oxide in Pulmonary Diseases: A Comprehensive Review," Chest, Official publication of the American College of Chest Physicians, 138/3, pp. 682-692, (2010).
Rollins, G., "Beyond Breathalyzers: What Clinical Niche Will Breath Tests Fill?" Clinical Laboratory News, vol. 37, No. 5, pp. 1-6, (2011).
U.S. Appl. No. 12/830,682—Non-Final Office Action, mailed Sep. 4, 2012, 21 pages.
U.S. Appl. No. 13/332,064—Non-Final Office Action, mailed Nov. 5, 2012, 24 pages.
U.S. Appl. No. 12/847,593—Non-Final Office Action, mailed Dec. 20, 2012, 6 pages.
Tian, W. et al., "Microfabricated Preconcentrator-Focuser for a Microscale Gas Chromatograph," Journal of Microelectromechanical Systems, vol. 12, No. 3, Jun. 2003, pp. 264-272.
CN 200980123127.X—First Chinese Office Action, mailed Feb. 28, 2013, 27 pages.
A. Hansel et al., "Proton transfer reaction mass spectrometry: on-line trace gas analysis at the ppb level," International Journal of Mass Spectrometry and Ion Processes, vols. 149-150, Nov. 15, 1995, pp. 609-619.
Auble, D.L. et al., "An open path, fast response infrared absorption gas analyzer for H2O and CO2," Boundary-Layer Meteorology, 1992, vol. 59, pp. 243-256.

(56) References Cited

OTHER PUBLICATIONS

Y. Aimin et al., "Analysis of Gas by a Portable Gas Chromatograph With a Microwave Induced Plasma Ionization Detector," Chinese Journal of Analytical Chemistry, 1993, vol. 21, No. 6, pp. 736-739, w/ Abstract.
Y. Haiying et al., "A New GC System for the Analysis of Permanent Gases," Rock and Mineral Analysis, Mar. 1999, vol. 18, No. 1, pp. 29-33, Beijing China (w/ Abstract).
B. Shi, "Application of 4 200 Ultra-fast GC Analyzer to Environment Emergence Monitoring," Liaoning Urban and Rural Environmental Science & Technology, 2006, vol. 26, No. 6, pp. 34-35 (w/ Abstract).
CN 2010-80031094.9—First Chinese Office Action, mailed Sep. 12, 2013, 15 pages.
U.S. Appl. No. 12/847,593—Final Office Action, mailed Jul. 18, 2013, 8 pages.
U.S. Appl. No. 12/830,682—Final Office Action, mailed Apr. 29, 2013, 22 pages.
U.S. Appl. No. 13/332,064—Non-Final Office Action, mailed Jun. 7, 2013, 23 pages.
CN 2009-80123127.X—Second Chinese Office Action, mailed Sep. 16, 2013, 13 pages.
EP 10 79 7800—EPO Communication pursuant to Article 153(7) EPC, dated Sep. 25, 2013, 6 pages.
JP 2011-514674—First Japanese Office Action, mailed Nov. 12, 2013, 5 pages.
CN 2010-80040138.4—First Chinese Office Action, mailed Oct. 28, 2013, 13 pages.
U.S. Appl. No. 12/847,593—Notice of Allowance, mailed Nov. 19, 2013, 11 pages.
U.S. Appl. No. 13/332,064—Notice of Allowance, mailed Nov. 25, 2013, 12 pages.
CN 2011-80026437.7—First Chinese Office Action, issued Jan. 6, 2014, 20 pages.
Liu Juntao et al., "Multi-Dimensional Gas Chromatography for Analysis of Refinery Gas," Modern Instruments, vol. 6, pp. 48-51.
CN 2010-80040138.4—Notice of Allowance, mailed Feb. 20, 2014, 13 pages.
U.S. Appl. No. 12/830,682—Non-Final Office Action, mailed Sep. 19, 2013, 22 pages.
CN 2009-80123127.X—Office Action, mailed May 15, 2014, 12 pages.
CN 2011-514674—Notice of Allowance, issued Jun. 19, 2014, 3 pages.
U.S. Appl. No. 14/678,380—Non-Final Office Action, mailed Jul. 27, 2016, 10 pages.
U.S. Appl. No. 14/659/212—Non-Final Office Action, mailed Sep. 22, 2016, 12 pages.
Philips, J.B. et al., "Comprehensive Multi-Dimensional Gas Chromatography", Journal of Chromatography A, vol. 703, 1995. pp. 327-334.
CN 2010-80031094.9—Second Chinese Office Action, issued Jun. 10, 2014, 29 pages.
Zhaobin Zhang, "Technique and Device for Analysis and Test," Series Double Column Chromatographic Analysis of Syngas Product After the Partial Oxidation of Methane at a Time, Jun. 30, 1998, pp. 1-32.
TW 099122362—First Office Action with English Translation, issued Aug. 12, 2014, 19 pages.
CN 2011-80026437.7—Second Chinese Office Action, issued Aug. 26, 2014, 24 pages.
TW 099125678—First Office Action with English Translation, issued Oct. 15, 2014, 15 pages.
U.S. Appl. No. 13/089,850—Notice of Allowance, mailed Nov. 6, 2014, 6 pages.
U.S. Appl. No. 12/830,682—Notice of Allowance, mailed Oct. 30, 2014, 5 pages.
U.S. Appl. No. 13/089,850—Non-Final Office Action, mailed Jul. 7, 2014, 49 pages.
EP 11772674.5—EPO Partial Supplementary European Search Report, dated Jan. 16, 2015, 11 pages.
CN 2010-80031094.9—Third Chinese Office Action, issued Jan. 29, 2015, 26 pages.
Grob, Konrad, "Split and Splitless Injection for Quantitative Gas Chromatography: Concepts, Processes, Practical Guidelines, Sources of Error", Dec. 13, 2007, XP-002733956, Chapter 4/D, pp. 339-400.
JP 2014-149768—First Japanese Office Action, mailed Apr. 24, 2015, 5 pages.
U.S. Appl. No. 12/830,682—Final Office Action, mailed Aug. 18, 2014, 16 pages.
TW 099122362—Second Office Action with English Translation, issued Apr. 24, 2015, 10 pages.
CN 2014-10138789.7—First Chinese Office Action, issued Feb. 2, 2015, 10 pages.
CN 2011-80026437.7—Third Chinese Office Action, issued May 4, 2015, 34 pages.
CN 2014-10554013.3—First Office Action with English Translation, issued Aug. 4, 2015, 12 pages.
CN 2010-80031094.9—Fourth Office Action with English Translation, issued Sep. 18, 2015, 35 pages.
CN 2014-10138789.7—Second Office Action with English Translation, issued Oct. 20, 2015, 5 pages.
TW 100114151—First Office Action, issued Aug. 6, 2015, 17 pages.
EP 11772674.5—EPO Extended European Search Report, dated Jun. 22, 2015, 23 pages.
CN 2011-80026437.7—Fourth Chinese Office Action, issued Dec. 3, 2015, 4 pages.
TW 099125678—Second Office Action with English Translation, issued Feb. 24, 2015, 8 pages.
CN 2014-10138789.7—Second Chinese Office Action, issued Oct. 20, 2015, 6 pages.
U.S. Appl. No. 14/678,380—Non-Final Office Action, mailed Oct. 6, 2015, 15 pages.
JP 2011-514674—Notice of Allowance, issued Jun. 19, 2014, 3 pages.
CN 2014-10554013.3—Second Office Action with English Translation, issued Feb. 22, 2016, 11 pages.
TW 099122362—Third Office Action with English Translation, issued Jun. 24, 2016, 4 pages.
CN 2010-80031094.9—Notice of Allowance with English Translation, Issued May 20, 2016, 4 pages.
TW 105129538—First Office Action with English Translation, issued Dec. 7, 2016, 4 pages.
European Patent Application No. 10805181.4—Extended European Search Report and Opinion, mailed Dec. 7, 2016, 10 pages.
Kim, Hanseup et al., "A Micropump-Driven High-Speed MEMS Gas Chromatography System", Solid-State Sensors, Actuators and Mirosystems Conference, 2007. Transducers 2007. Jun. 10, 2007, pp. 1505-1508.
M. Agah et al., "High-Speed MEMS-Based Gas Chromatography", Journal of Microelectromechanical Systems., vol. 15, No. 5, Oct. 2006, pp. 1371-1378.
Edward T. Zellers et al., "An Integrated Micro-Analytical System for Complex Vapor Mixtures", Solid-State Sensors, Actuators and Microsystems Conference, 2007. Sep. 24, 2007, pp. 1491-1496.

\* cited by examiner

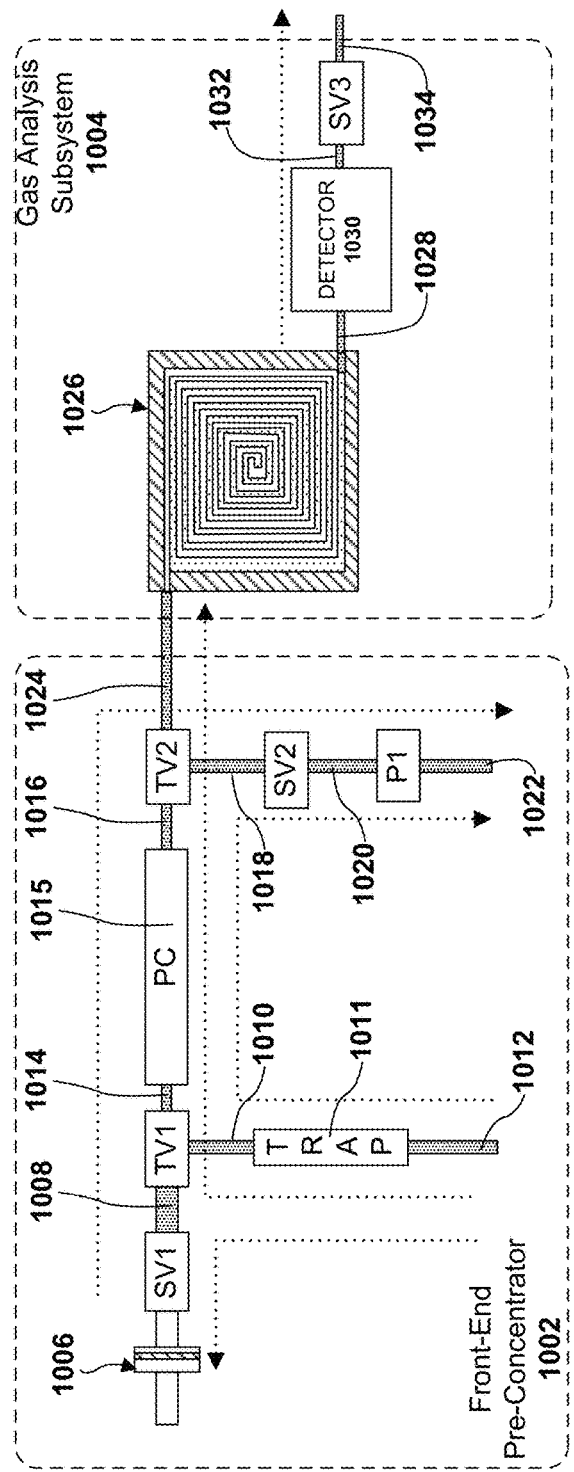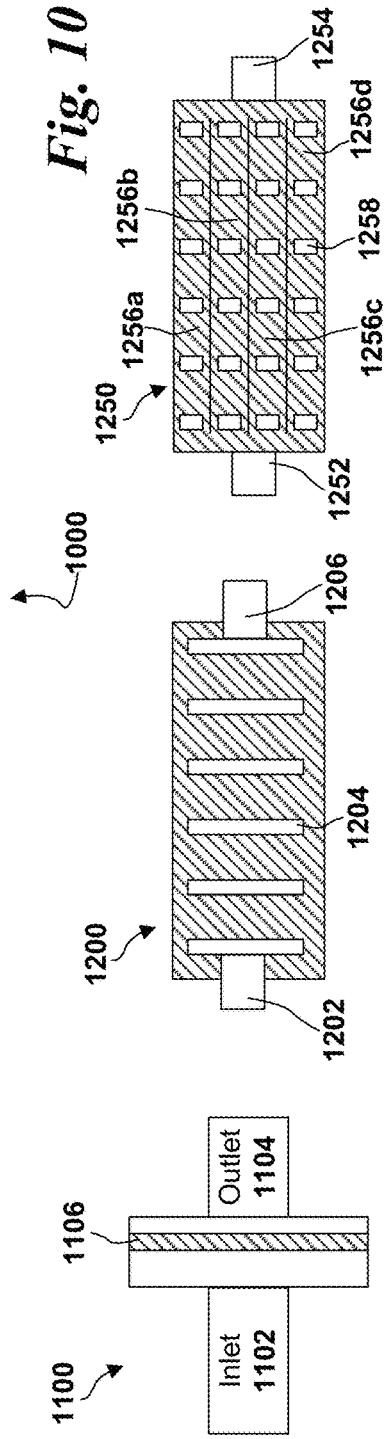
Fig. 10
Fig. 11
Fig. 12A
Fig. 12B

GAS COLLECTION AND ANALYSIS SYSTEM WITH FRONT-END AND BACK-END PRE-CONCENTRATORS AND MOISTURE REMOVAL

CROSS-REFERENCE TO RELATED APPLICATIONS

This application is a continuation of its parent application, U.S. application Ser. No. 12/847,593, filed 30 Jul. 2010 and still pending, and claims priority thereto under 35 U.S.C. §120. The parent application in turn claims priority under 35 U.S.C. §119(e) to U.S. Provisional Patent Application No. 61/230,647, filed 31 Jul. 2009, and U.S. Provisional Patent Application No. 61/326,433, filed 21 Apr. 2010. Both provisional applications are incorporated herein by reference in their entirety.

TECHNICAL FIELD

The present invention relates generally to gas analysis systems and in particular, but not exclusively, to handheld gas analysis systems including front-end pre-concentrators, back-end pre-concentrators and moisture removal.

BACKGROUND

Gas analysis can be an important means for detecting the presence and concentration of certain chemicals in the gas and determining the meaning of the particular combination of chemicals present. In health care, for example, the presence of certain volatile organic compounds (VOCs) in exhaled human breath are correlated to certain diseases, such as pneumonia, pulmonary tuberculosis (TB), asthma, lung cancer, liver diseases, kidney diseases, etc. The correlations are especially evidential for lung-related diseases. In other applications, gas analysis can be used to determine the presence of dangerous substances incompatible with human presence, such as methane, carbon monoxide or carbon dioxide in a mine.

Current gas analytical systems still rely heavily on large and expensive laboratory instruments, such as gas chromatography (GC) and mass spectrometry (MS). Most of these instruments (mass spectrometers in particular) have operational characteristics that prevent significant reductions in their size, meaning that current gas analysis systems are large and expensive bench devices. In addition to being expensive and unwieldy, the large size of current gas analysis devices makes widespread use of these instruments impossible.

Since the conventional GC/MS are bulky in size and expensive, the equipment is usually located in the labs and breath samples must be collected in the laboratories or by other on-site means. Two approaches have been used for on-site breath collection. The canister breath collection is the most commonly used approach: breath is inhaled and collected into a pre-cleaned and pre-vacuumed bottle, and the bottle is then sent to a lab for analysis. Such canisters are very expensive and also require a very expensive cleaning system in order to re-use the canister. As a result, the breath test cost cannot be reduced due to very high cost in equipment and system setup. In another approach, instead of using a canister, a trap is used as an alternative on-site breath collection: the trap is located in a breath collection system, which monitors the amount of breath and condition during collection. The trap is then removed and then sent to lab for analysis using similar gas analysis equipment for the canister approach. The trap approach eliminates the requirement of expensive cleaning tools, but the trap collection system itself can be more expensive than the canister. Both breath collection and analysis approaches requires the breath collection on-site and then the samples are sent back to labs for analysis, which is time-consuming and very expensive.

Exhaled breath contains >90% humidity. When the moisture is collected together with gases/volatile organic compounds (VOCs) from breath and then directly injected into a gas analysis system, any significant amount of moisture will drastically reduce the analyzer sensitivity to chemicals/VOCs of interest. As a result, the system's detection limit becomes much worse than the case when there is no or low moisture present. The current approach in moisture removal for breath analysis is to extract the collected breath sample from the container, which is used to store breath from the subject. The sample is then extracted and injected into a front-end moisture removal equipment. The equipment cools down (condenses) the collected breath (including moisture) in a trap or tube to sub-zero Celsius temperature (by liquid nitrogen or dry ice) and then heats up the trap to separate moisture from other gases due to different boiling temperatures. There can be multiple stages of cryo-cooling and heating steps to remove moisture before gases/VOCs are transferred into a gas chromatograph/mass spectrometer (GC/MS) system for analysis. Such front-end equipment is massive in size and highly expensive (>$20,000).

The existing approach requires expensive equipment setup and is bulky in size as described above. The breath analysis is performed in multiple stages. Breath first is collected in canister, trap, or other container. The sample is then transferred to laboratory, where the moisture removal system (front-end system) and gas/VOC analysis system (e.g., GC/MS) are located. The gases/VOCs and moisture are then extracted from the sample to the front-end system for moisture removal before the gases/VOCs are fed into the analyzer (GC/MS). The equipment is expensive and not portable. Meanwhile, this breath collection and moisture removal procedure cannot be used for in-situ breath analysis.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 10 is a schematic diagram of an embodiment of a gas analysis device including a front-end pre-concentrator module.

FIG. 11 is a drawing of an embodiment of a filter assembly that can be used with a gas analysis device.

FIG. 12A is a drawing of an embodiment of a pre-concentrator that can be used with an embodiment of a gas analysis system.

FIG. 12B is a drawing of an alternative embodiment of a pre-concentrator that can be used with an embodiment of a gas analysis system.

DETAILED DESCRIPTION OF THE ILLUSTRATED EMBODIMENTS

Embodiments of an apparatus, process and system for gas analysis in point-of-care medical applications are described herein. In the following description, numerous specific details are described to provide a thorough understanding of embodiments of the invention. One skilled in the relevant art will recognize, however, that the invention can be practiced without one or more of the specific details, or with other methods, components, materials, etc. In other instances, wellknown structures, materials, or operations are not shown or described in detail but are nonetheless encompassed within the scope of the invention.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in this specification do not necessarily all refer to the same embodiment. Furthermore, the particular features, structures, or characteristics may be combined in any suitable manner in one or more embodiments.

Figure 1A:
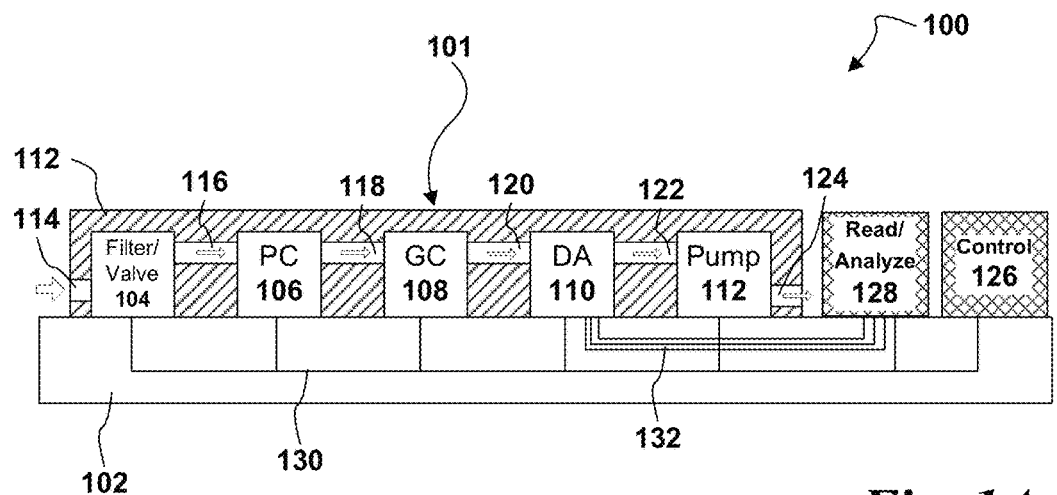
FIG. 1A is a side elevation drawing of an embodiment of a gas analysis device.
Figure 1B:
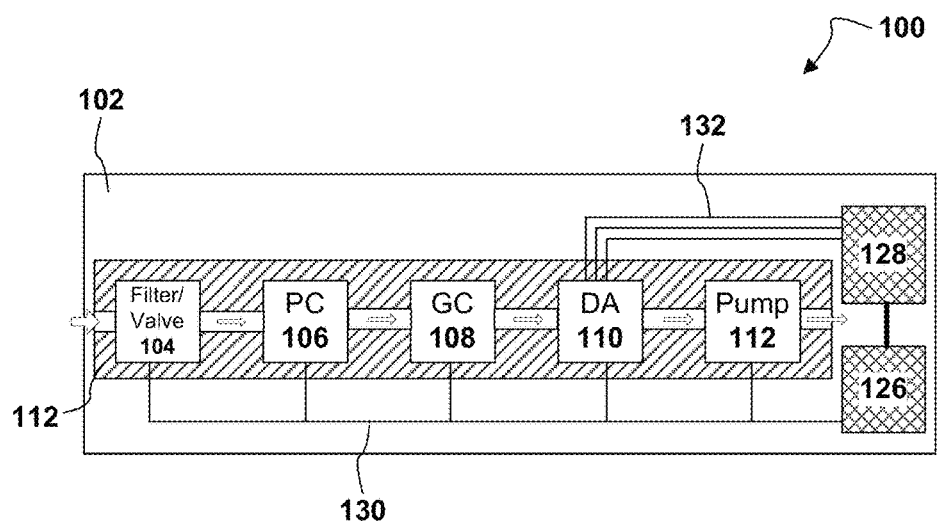
FIG. 1B is a plan view of the embodiment of a gas analysis device shown in FIG. 1.

FIGS. 1A and 1B together illustrate an embodiment of a small scale (e.g., handheld) gas analysis device 100. Device 100 includes a substrate 102 on which are mounted a fluid handling assembly 101, a controller 126 coupled to the individual elements within fluid handling assembly 101, and a reading and analysis circuit 128 coupled to detector array 110 and to controller 126. The embodiment shown in the figures illustrates one possible arrangement of the elements on substrate 102, but in other embodiments the elements can, of course, be arranged on the substrate differently.

Substrate 102 can be any kind of substrate that provides the required physical support and communication connections for the elements of device 100. In one embodiment, substrate 102 can be a printed circuit board (PCB) of the single-layer variety with conductive traces on its surface, but in other embodiments it can be a PCB of the multi-layer variety with conductive traces in the interior of the circuit board. In other embodiments, for example an embodiment where device 100 is built as a monolithic system on a single die, substrate 102 can be chip or wafer made of silicon or some other semiconductor. In still other embodiments, substrate 102 can also be a chip or wafer in which optical waveguides can be formed to support optical communication between the components of device 100.

Fluid handling assembly 101 includes a filter and valve assembly 104, a pre-concentrator 106, a gas chromatograph 108, a detector array 110 and a pump 112. Elements 104-112 are fluidly coupled in series: filter and valve assembly 104 is fluidly coupled to pre-concentrator 106 by fluid connection 116, pre-concentrator 106 is fluidly coupled to gas chromatograph 108 by fluid connection 118, gas chromatograph 108 is fluidly coupled to detector array 110 by fluid connection 120, and detector array 110 is coupled to pump 112 by fluid connection 122. As further described below, in one embodiment of device 100 elements 104-112 can be micro-electro-mechanical (MEMS) elements or MEMS-based elements, meaning that some parts of each device can be MEMS and other parts not. In other embodiments of device 100, some or all of elements 104-112 need not be MEMS or MEMS-based, but can instead be some non-MEMS chip scale device.

As indicated by the arrows in the figures, the fluid connections between elements 104-112 allow a fluid (e.g., one or more gases) to enter filter and valve assembly 104 through inlet 114, flow though elements 104-112, and finally exit pump 112 through outlet 124. Fluid handling assembly 101 also includes a shroud or cover 112 that protects individual elements 104-112. In the illustrated embodiment, channels formed in shroud 112 provide the fluid connections between the elements, but in other embodiments the fluid connections between elements can be provided by other means, such as tubing. In still other embodiments shroud 112 can be omitted.

Filter and valve assembly 104 includes an inlet 114 and an outlet coupled to fluid connection 116 such that fluid exiting filter and valve assembly 104 flows into pre-concentrator 110. Filter and valve assembly 104 includes a filter to remove particulates from fluid entering through inlet 114. In embodiments of device 100 where one or more of elements 104-112 is a MEMS element, the small scale of parts within the MEMS elements of device pre-concentrator means that fluid entering through inlet 114 can be filtered to remove these particles so that the particles do not enter the MEMS devices and either damage them or render them inoperative. In embodiments of device 100 that include no MEMS components or where fluid entering inlet 114 contains no particles, for instance because it has been pre-filtered externally to device 100, the filter portion of filter and valve assembly 104 can be omitted.

Filter and valve assembly 104 also includes a valve so that further flow through inlet 114 into fluid handling assembly 101 can be stopped once sufficient fluid has passed through the device. Stopping further flow through inlet 114 prevents dilution of fluids that will flow out of pre-concentrator 106 during later operation of device 100 (see description of operation below). In other embodiments, filter and valve assembly 104 can also include a de-humidifier to remove water vapor from the fluid entering through inlet 114, thus improving the accuracy and sensitivity of device 100.

Pre-concentrator 106 includes an inlet coupled to fluid connection 116 and an outlet coupled to fluid connection 118. Pre-concentrator 106 receives fluid from filter and valve assembly 104 through fluid connection 116 and outputs fluid to gas chromatograph 108 through fluid connection 118. As fluid flows through pre-concentrator 106, the pre-concentrator absorbs certain chemicals from the passing fluid, thus concentrating those chemicals for later separation and detection. In one embodiment of device 100 pre-concentrator 106 can be a MEMS pre-concentrator, but in other embodiments pre-concentrator 106 can be a non-MEMS chip scale device. Further details of an embodiment of a MEMS pre-concentrator are described below in connection with FIG. 2.

Gas chromatograph 108 includes an inlet coupled to fluid connection 118 and an outlet coupled to fluid connection 120. Gas chromatograph 108 receives fluid from pre-concentrator 106 through fluid connection 118 and outputs fluid to detector array 110 through fluid connection 120. As fluid received from pre-concentrator 106 flows through gas chromatograph 108, individual chemicals in the fluid received from the pre-concentrator are separated from each other in the time domain for later input into detector array 110. In one embodiment of device 100 gas chromatograph 108 can be a MEMS gas chromatograph, but in other embodiments gas chromatograph 108 can be a non-MEMS chip scale device. Further details of an embodiment of a MEMS gas chromatograph 108 are described below in connection with FIGS. 3A-3B.

Detector array 110 includes an inlet coupled to fluid connection 120 and an outlet coupled fluid connection 122. Detector array 110 receives fluid from gas chromatograph 108 through fluid connection 120 and outputs fluid to pump 112 through fluid connection 122. As fluid flows through detector array 110, the chemicals that were time-domain separated by gas chromatograph 108 enter the detector array and their presence and/or concentration is sensed by sensors within the detector array. In one embodiment of device 100 detector array 110 can be a MEMS detector array, but in other embodiments detector array 110 can be a non-MEMS chip scale device. Further details of an embodiment of a detector array 110 are described below in connection with FIG. 4.

Pump 112 includes an inlet coupled to fluid connection 122, as well as an outlet coupled to an exhaust 124, such that pump 112 draws fluid from detector array 110 through fluid connections 122 and returns it to the atmosphere through exhaust 124. Pump 112 can be any kind of pump that meets the size and form factor requirements of device 100, provides the desired flow rate and flow rate control, and has adequate reliability (i.e., an adequate mean time between failures (MTBF)). In one embodiment, pump 112 can be a MEMS or MEMS-based pump, but in other embodiments it can be another type of pump. Examples of pumps that can be used include small axial pumps (e.g., fans), piston pumps, and electro-osmotic pumps.

Controller 126 is communicatively coupled to the individual elements within fluid handling assembly 101 such that it can send control signals and/or receive feedback signals from the individual elements. In one embodiment, controller 126 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of fluid handling assembly 101. In other embodiments, however, controller 126 can instead be a general-purpose microprocessor in which the control functions are implemented in software. In the illustrated embodiment controller 126 is electrically coupled to the individual elements within fluid handling assembly 101 by conductive traces 130 on the surface or in the interior of substrate 102, but in other embodiments controller 126 can be coupled to the elements by other means, such as optical.

Readout and analysis circuit 128 is coupled to an output of detector array 110 such that it can receive data signals from individual sensors within detector array 110 and process and analyze these data signals. In one embodiment, readout and analysis circuit 128 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, however, readout and analysis circuit 128 can instead be a general-purpose microprocessor in which the control functions are implemented in software. In some embodiments readout and analysis circuit 128 can also include signal conditioning and processing elements such as amplifiers, filters, analog-to-digital converters, etc., for both pre-processing of data signals received from detector array 110 and post-processing of data generated or extracted from the received data by readout and analysis circuit 128.

In the illustrated embodiment, readout and analysis circuit 128 is electrically coupled to detector array 110 by conductive traces 132 positioned on the surface or in the interior of substrate 102, but in other embodiments controller 126 can be coupled to the elements by other means, such as optical means. Readout and analysis circuit 128 is also coupled to controller 126 and can send signals to, and receive signals from, controller 126 so that the two elements can coordinate and optimize operation of device 100. Although the illustrated embodiment shows controller 126 and readout and analysis circuit 128 as physically separate units, in other embodiments the controller and the readout and analysis circuit could be combined in a single unit.

In operation of device 100, the system is first powered up and any necessary logic (i.e., software instructions) is loaded into controller 126 and readout and analysis circuit 128 and initialized. After initialization, the valve in filter and valve unit 104 is opened and pump 112 is set to allow flow through the fluid handling assembly. Fluid is then input to fluid handling assembly 101 through inlet 114 at a certain flow rate and/or for a certain amount of time; the amount of time needed will usually be determined by the time needed for pre-concentrator 106 to generate adequate concentrations of the particular chemicals whose presence and/or concentration are being determined. As fluid is input to the system through inlet 114, it is filtered by filter and valve assembly 104 and flows through elements 104-112 within fluid handling assembly 101 by virtue of the fluid connections between these elements. After flowing through elements 104-112, the fluid exits the fluid handling assembly through exhaust 124.

After the needed amount of fluid has been input through inlet 114, the valve in filter and valve assembly 104 is closed to prevent further input of fluid. After the valve is closed, a heater in pre-concentrator 106 activates to heat the pre-concentrator. The heat releases the chemicals absorbed and concentrated by the pre-concentrator. As the chemicals are released from pre-concentrator 106, pump 112 is activated to draw the released chemicals through gas chromatograph 108 and detector array 110 and output the chemicals through exhaust 124. Activation of pump 112 also prevents backflow through fluid handling assembly 101.

As the chemicals released from pre-concentrator 106 are drawn by pump 112 through gas chromatograph 108, the chromatograph separates different chemicals from each other in the time domain—that is, different chemicals are output from the gas chromatograph at different times. As the different chemicals exit gas chromatograph 108 separated in time, each chemical enters MEMS detection array 110, where sensors in the detection array detect the presence and/or concentration of each chemical. The time-domain separation performed in gas chromatograph 108 substantially enhances the accuracy and sensitivity of MEMS detection array 110, since it prevents numerous chemicals from entering the detection array at the same time and thus prevents cross-contamination and potential interference in the sensors within the array.

As individual sensors within MEMS detection array 110 interact with the entering time-domain-separated chemicals, the detection array senses the interaction and outputs a signal to readout and analysis circuit 128, which can then use the signal to determine presence and/or concentration of the chemicals. When readout and analysis circuit 128 has determined the presence and/or concentration of all the chemicals of interest it can use various analysis techniques, such as correlation and pattern matching, to extract some meaning from the particular combination of chemicals present and their concentrations.

Figure 2A:
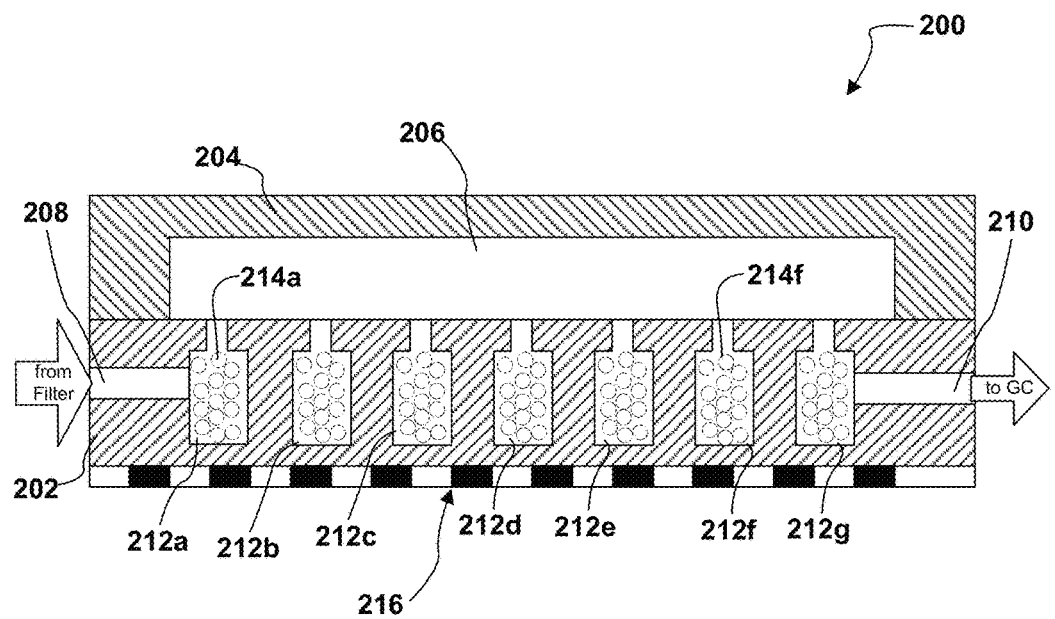
FIG. 2A is a cross-sectional elevation drawing of an embodiment of a MEMS pre-concentrator that can be used in the embodiment of a gas analysis device shown in FIGS. 1A-1B.

FIG. 2A illustrates an embodiment of a MEMS pre-concentrator 200 that can be used as pre-concentrator 106 in device 100. Pre-concentrator 200 includes a substrate 202 having a cover plate 204 bonded thereto and sealed around the perimeter of the substrate to create a cavity 206. Substrate 202 has formed therein an inlet 208 on one side, an outlet 210 on a different side, and pockets 212 having absorbents therein. In one embodiment, substrate 202 is a silicon substrate, but in other embodiments substrate 202 can of course be made of other materials. Heater 216 is formed on the side of substrate 202 opposite the side where cover plate 204 is attached.

In an embodiment where substrate 202 is silicon, inlet 208, outlet 210 and pockets 212 can be formed using standard photolithographic patterning and etching. Although the illustrated embodiment shows seven pockets 212a-212g, the number of pockets needed depends on the number of different chemicals to be absorbed and concentrated, and on the nature of the absorbents used. In an embodiment where each absorbent absorbs only one chemical, the number of pockets 212 can correspond exactly to the number of chemicals to be absorbed and concentrated, but in other embodiments where each absorbent absorbs only one chemical a greater number of pockets can be used to increase the absorption area. In still other embodiments where each absorbent can absorb more than one chemical, a lesser number of pockets can be used.

Each pocket 212 has a corresponding absorbent 214 in its interior—pocket 212a has absorbent 214a, pocket 212b has absorbent 214b, and so on. Although shown in the illustrated embodiment as a granular absorbent, in other embodiments absorbents 214 can be coatings on the walls of pockets 212 or can be a continuous substance that partially or fully fills each pocket 212. Other embodiments can include combinations of granular, wall coatings or continuous filling absorbents. Each absorbent can have a chemical affinity for one or more particular chemicals, meaning that the exact absorbents used will depend on the number and nature of chemicals to be absorbed and concentrated. Examples of absorbents that can be used include cabopack B, cabopack X, etc.

During operation of MEMS pre-concentrator 200 in device 100, fluid from filter and valve assembly 104 enters through inlet 208, passes through absorbent 214a in pocket 212a, and enters cavity 206. Cover plate 204 helps guide fluid entering the cavity 206 into the different pockets 212b-212g and through absorbents 214b-214g, until the fluid, minus the chemicals absorbed by absorbents 214a-214g, exits the pre-concentrator through outlet 210. Once enough fluid has flowed through the pre-concentrator, the valve in filter and valve assembly 104 is closed to prevent further flow through inlet 208. Heater 216 is then activated. Heater 216 heats absorbents 214a-214f, causing them to release the absorbed chemicals through processes such as outgassing. Simultaneously with activating heater 216, or shortly thereafter, pump 112 is activated, drawing the released chemicals out through outlet 210 to gas chromatograph 108.

Figure 2B:
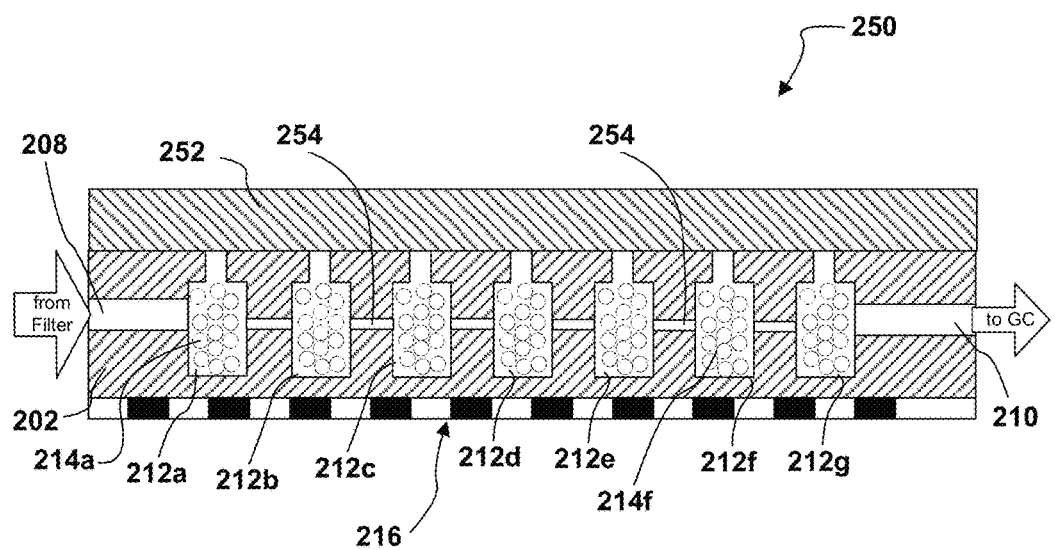
FIG. 2B is a cross-sectional elevation drawing of an alternative embodiment of a MEMS pre-concentrator that can be used in the embodiment of a gas analysis device shown in FIGS. 1A-1B.

FIG. 2B illustrates an alternative embodiment of a MEMS pre-concentrator 250. MEMS pre-concentrator 250 is in many respects similar to MEMS pre-concentrator 200. The primary difference between the two is that in MEMS pre-concentrator 250, the cover plate 252 is directly bonded to the substrate 202 without formation of cavity 206 found in cover plate 204. In one embodiment of MEMS pre-concentrator 250, channels/openings 252 can exist in substrate 202 between the different pockets 212 to allow the fluid to flow through adjacent pockets. In operation of MEMS pre-concentrator 250, fluid enters through inlet 208, passes through the different pockets 212a-212g via the channels/openings 252 between the pockets, and finally exits the pre-concentrator through outlet 210.

Figure 3A:
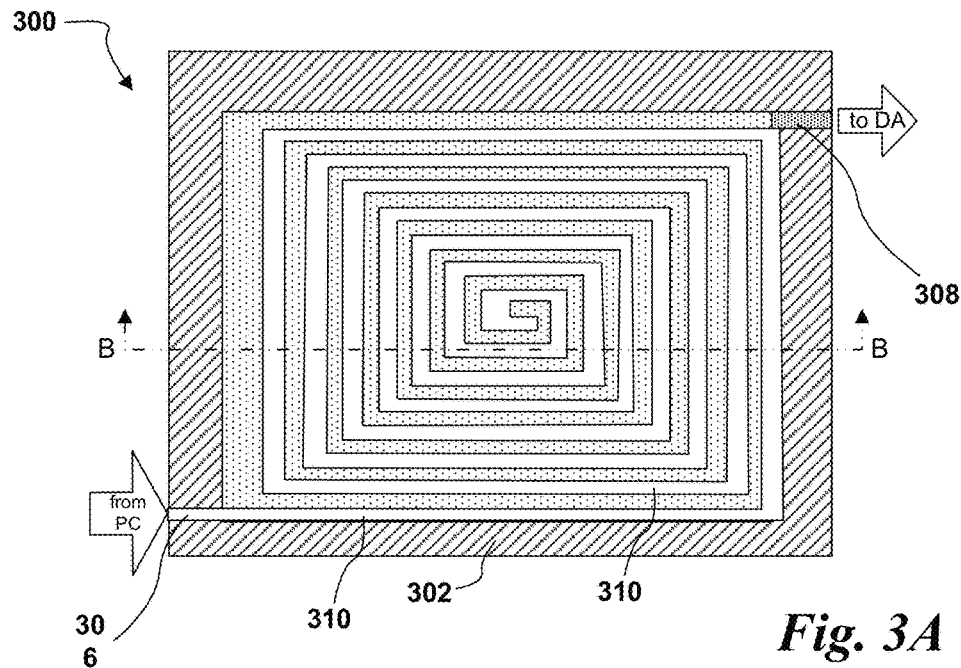
FIG. 3A is a plan view drawing of an embodiment of a MEMS gas chromatograph that can be used in the embodiment of a gas analysis device shown in FIGS. 1A-1B
Figure 3B:
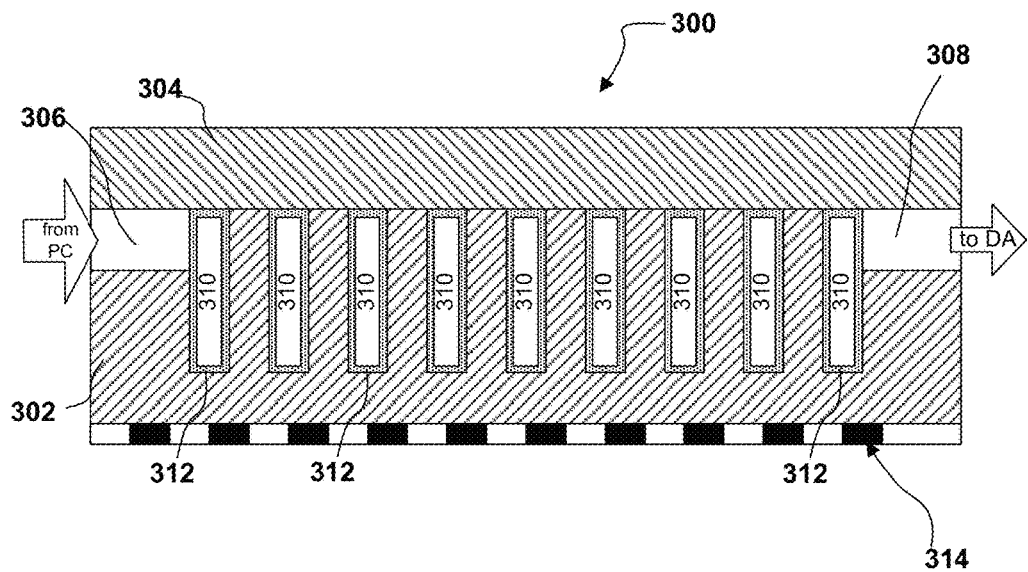
FIG. 3B is a cross-sectional elevation drawing of the embodiment of a MEMS gas chromatograph shown in FIG. 3A, taken substantially along section line B-B.

FIGS. 3A-3B illustrate an embodiment of a MEMS gas chromatograph 300 that can be used as gas chromatograph 108 in device 100. MEMS gas chromatograph 300 includes a substrate 302 with an inlet 306 on one side, an outlet 308 on a different side, and a separation column 310 having a stationary phase coating on its walls. A cover plate 304 is bonded to substrate 302 to seal column 310. In one embodiment substrate 302 is a silicon substrate, but in other embodiments substrate 302 can of course be made of other materials. In an embodiment where substrate 302 is silicon, inlet 306, outlet 308 and column 310 can be formed using standard photolithographic patterning and etching, such as deep reactive ion etching (DRIE). Heater 314 is formed on the side of substrate 302 opposite the side where cover plate 204 is attached.

Column or channel 310 provides a continuous flow path from inlet 306 to outlet 308, and some or all of the walls of column 310 are coated with a stationary phase coating that can interact with the chemicals being separated by the chromatograph or, in other words, the column walls are coated with specific materials that have specific selectivity/separation power for the desired gas analysis. How thoroughly and how fast chemicals are separated from the fluid depend on the stationary phase coating, the overall path length of column 310, and the temperature. For a given stationary phase coating, the longer the column the better the chemical spectrum separation, but a long column also extends the separation time. For a given application, the required path length will therefore usually be determined by a tradeoff among the coating, the column length and the temperature. The illustrated embodiment shows column 310 as a spiral column in which the column path length will depend on the number of coils in the spiral. In other embodiments, however, column 310 can be shaped differently. In one embodiment, column 310 can be between 1 m and 10 m in length, but in other embodiment can be outside this range. In the illustrated MEMS GC, column 310 can be formed by micromachining or micro-electro-mechanical-systems (MEMS) process on silicon wafer, glass wafer, PCB board, or any type of substrate.

During operation of MEMS gas chromatograph 300 in device 100, fluid from pre-concentrator 106 enters through inlet 306 and passes through column 310. As fluid passes through the column 310, the different chemicals in the fluid interact with stationary phase coating 312 at different rates, meaning that the chemicals are separated after traveling through the column, with the chemicals that interact strongly with the stationary phase being separated first and the chemicals that interact weakly with the stationary phase being separated last. In other words, chemicals that interact strongly with the stationary phase are retained longer in the stationary phase, while chemicals that interacted weakly with the stationary phase retained less time in the stationary phase. In some embodiments of gas chromatograph 300 this time-domain separation can occur according to molecular weight (e.g., chemicals with the lowest molecular weight are separated first, followed by higher molecular weights), but in other embodiments it can occur according to other chemical characteristics or other separation mechanisms. As the chemicals are time-domain separated, pump 112 draws them out of MEMS gas chromatograph 300 through outlet 308. Generally, the chemicals exit through outlet 308 in the reverse order of their separation—that is, chemicals with low retention time exit first, while chemicals with higher retention times exit later. After leaving outlet 308, the chemicals enter detector array 110.

Figure 4A:
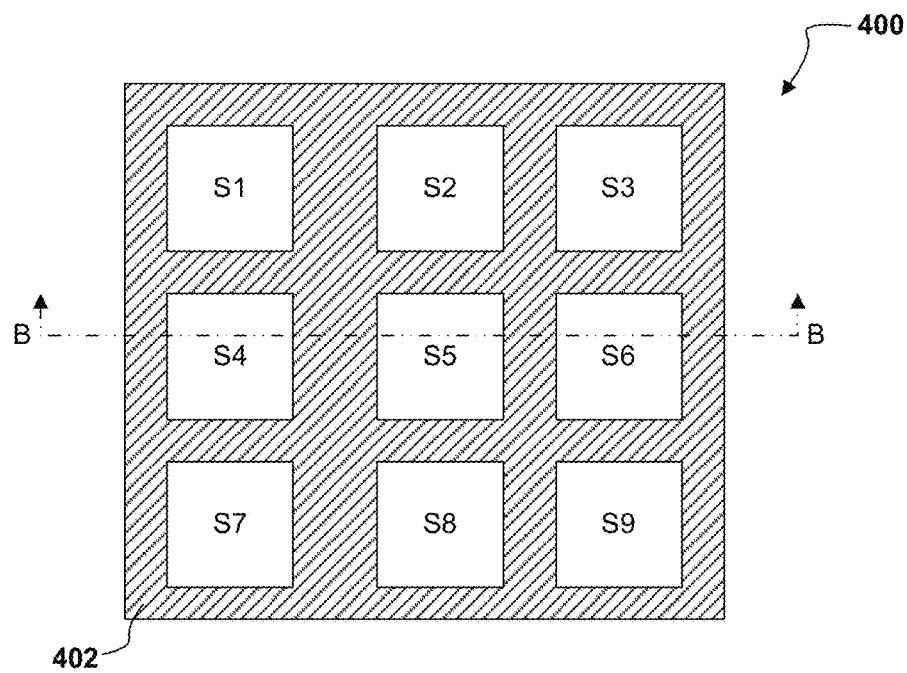
FIG. 4A is a plan view drawing of an embodiment of a detector array that can be used in the embodiment of a gas analysis device of FIGS. 1A-1B.
Figure 4B:
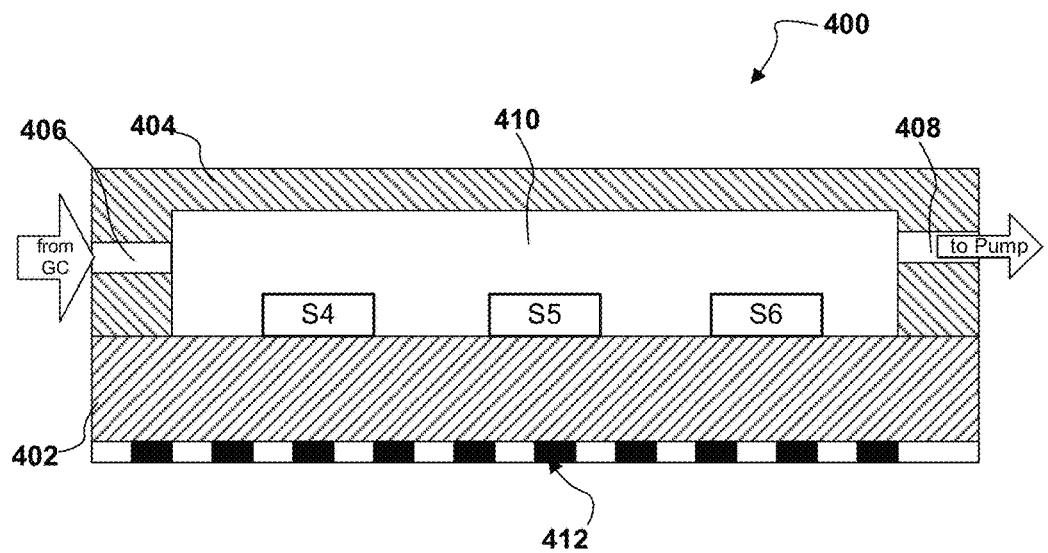
FIG. 4B is a cross-sectional elevation drawing of the embodiment of a detector array shown in FIG. 4A, taken substantially along section line B-B.

FIGS. 4A-4B illustrate an embodiment of a detector array 400 that can be used as detector array 110 in device 100. Detector array 400 includes a substrate 402 with an array of sensors S1-S9 formed thereon. In the illustrated embodiment sensors S1-S9 form a regularly shaped 3-by-3 array of sensors, but in other embodiments the sensor array can have a greater or lesser number of sensors, and the sensors can be arranged in any pattern, regular or irregular.

A cover 404 is bonded to the perimeter of substrate 402 to form a cavity 410 within which sensors S1-S9 are located. Cover 404 also includes an inlet 406 through which fluid can enter from gas chromatograph 108 and an outlet 408 through which fluid can exit to pump 112. A heater 412 is formed on the side of substrate 402 opposite the side where cover 404 is attached to control the temperature of detector array 400, and hence the sensors within the detector array, during operation. Although not shown in the figure, detector array 400 of course includes outputs by which signals generated by sensors S1-S9 can be output for processing.

Each sensor S1-S9 includes a surface with a coating thereon. Each coating used will have an affinity for one or more of the particular chemicals being detected, such that the coating absorbs or chemically interacts with its corresponding chemical or chemicals. The interaction between coating and chemical in turn changes a physical property of the sensor such as resonant frequency, capacitance or electrical resistance, and that changed physical property of the sensor can be measured using a transducer or other measurement device. The particular coatings chosen for sensors S1-S9 will depend on the chemicals that sensor array 110 will be used to detect. The chemical affinity of coatings also varies strongly with temperature, so that the operating temperature range should be considered in selecting coatings. In an embodiment where sensor array 110 will be used to detect volatile organic compounds in human breath—such as benzene, toluene, n-octane, ethylbenzene, m,p-xylene, α-pinene, d-limonene, nonanal, and benzaldehyde, 2-methylhexane, 4-methyloctane, and so on—coatings that can be used in different applications include amorphous copolymers of 2,2-bistrifluoromethyl-4,5-difluoro-1,3-dioxole (PDD) and tetrafluoroethylene (TFE), PtCl2 (olefin), C8-MPN, etc.

Although the illustrated embodiment has nine sensors, the number of sensors needed depends on the number of different chemicals to be detected, and on the nature of the coatings used on the sensors. In an embodiment where each coating absorbs or chemically interacts with only one chemical the number of sensors can correspond exactly to the number of chemicals to be detected, but in other embodiments it can be desirable to have a given coating on more than one sensor for redundancy. In most cases, however, there is no one-to-one correlation between chemicals to coatings; in other words, each coating reacts with more than one different chemical and the reaction between different chemicals and a given coating will vary in nature and strength. A detector array having sensors with different coatings is therefore useful because the response of the detector array can have different patterns for different gases.

In one embodiment of sensor array 400, sensors S1-S9 are MEMS sensors positioned on the surface of substrate 402, meaning that they are surface micromachined sensors. In other embodiments using MEMS sensors, however, sensors S1-S9 can be bulk micromachined sensors, meaning that at least some of the MEMS sensors are formed within substrate 402 instead of on the surface. Still other embodiments of sensor array 110 using MEMS sensors can include combinations of surface-micromachined and bulk-micromachined sensors. Different types of MEMS sensors can be used, depending on the application and the required sensitivity. Examples of MEMS sensors that can be used include chemiresistors, bulk acoustic wave (BAW) sensors, etc. In other embodiments of detector array 400, one or more of sensors S1-S9 can be a non-MEMS sensor. Examples of non-MEMS sensors that can be used in detector array 400 include quartz crystal microbalance (QCM) or surface acoustic wave (SAW) sensors with quartz or Gallium Arsenide (GaAs) substrates.

During operation of MEMS detector array 400 in device 100, fluid from gas chromatograph 108 enters through inlet 406 and passes into cavity 410. Fluid entering cavity 410 carries time-domain separated chemicals. As each chemical enters cavity 410 it interacts with one or more sensors whose coating has an affinity for that chemical. The interaction of the chemical with the sensor is sensed and measured, and the presence and concentration of the particular chemical can be extracted. As more fluid flows into cavity 410, the first chemical is pushed out of cavity 410 through outlet 408 and fluid with the next time-domain-separated chemical enters cavity 410, interacts with the sensor array and is measured. This process continues until all the time-domain-separated chemicals from gas chromatograph 108 have flowed through detector array 110. In some embodiments where the affinity of the coatings for their chemicals is not strong, detector array 110 can be re-usable: after all time-domain-separated chemicals have been sensed, heater 412 can be activated to heat the sensors and cause the coatings to release the respective chemicals with which they interacted, making the interaction reversible. In embodiments where the affinity of each coating for its chemicals could be strong, heating of the sensor array could help release the partially absorbed gas from the coating materials.

Figure 5:
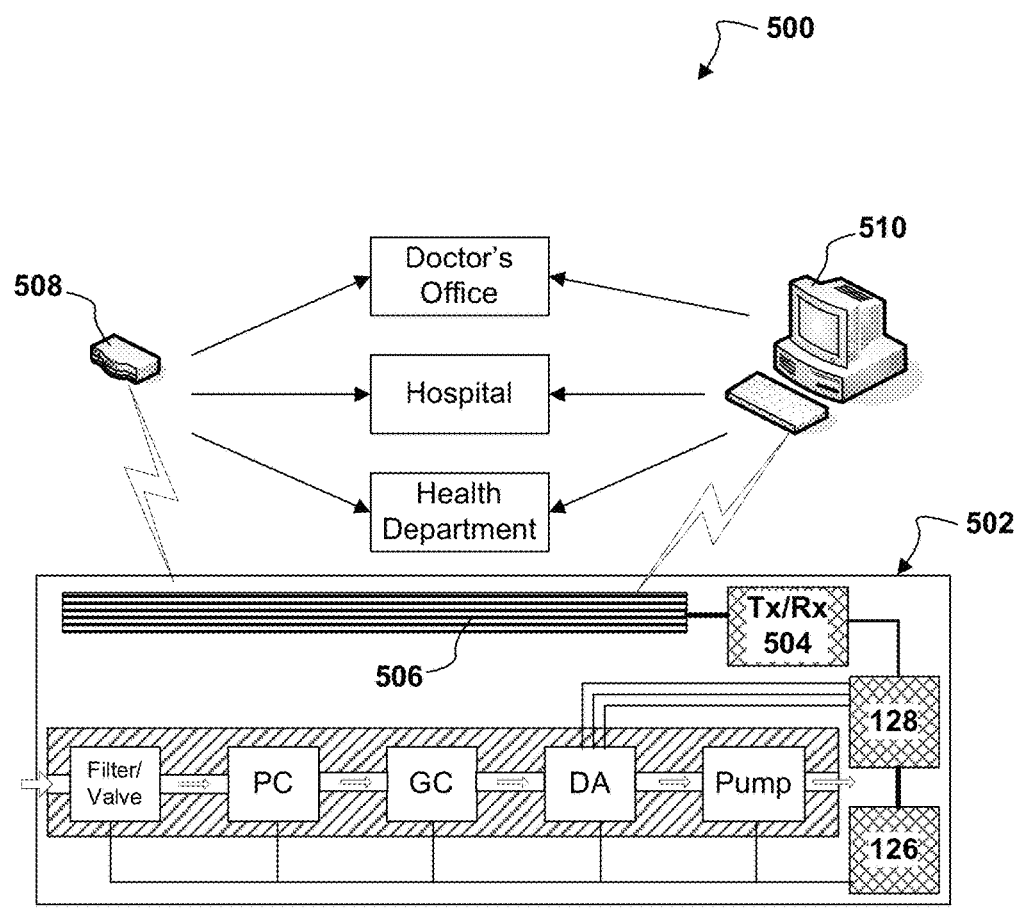
FIG. 5 is a schematic diagram of an alternative embodiment of a gas analysis device and an embodiment of a system using the embodiment of the gas analysis device.

FIG. 5 illustrates an embodiment of a system 500 using an alternative embodiment of a MEMS-based gas analysis device 502. Device 502 is in most respects similar to device 100. The primary difference between device 502 and device 100 is the presence in device 502 of a wireless transceiver circuit 504 and an antenna 506 mounted on substrate 102. Wireless transceiver circuit 504 can both transmit (Tx) data and receive (Rx) data and is coupled to reading and analysis circuit 128 and antenna 506.

In one embodiment of system 500, transceiver 504 can be used to wirelessly transmit raw data from reading and analysis circuit 128 to one or both of a router 508 and a computer 510. When transmitted to router 508, the data can then be re-transmitted to another destination for analysis. For example, in an application where device 502 is used for health-related chemical analysis, data sent to router 508 can be re-transmitted to one or more of a doctor's office, a hospital, a government health department, or someplace else for analysis and interpretation. After analysis is complete, or if there is a problem with the data, the doctor's office, hospital or health department can send instructions to device 502 through router 508, antenna 506 and transceiver 504 to signal the result, to try to fix or improve the data, or to signal that the test must be performed again.

Continuing with the same health-care example, in the same or another embodiment of system 500, wireless transceiver 504 can be used to transmit raw data to computer 510. Computer 510 can either forward the raw data to a doctor, hospital, etc., as did the router, or can analyze the data with software installed thereon to provide extract information from the data, such as one or more possible medical diagnoses, and provide the extracted information to the user of device 502. When it provides analysis and medical diagnoses, computer 510 can also forward the diagnosis, alone or with the analysis and raw data, on to the doctor, hospital, etc. As with the router, the doctor's office, hospital or health department can send instructions to device 502 through computer 510, antenna 506 and transceiver 504 to try to fix or improve the data, to signal that the test must be performed again, and so on.

Again continuing with the same health-care example, in still another embodiment of system 500 the raw data can be processed, and information such as potential diagnoses extracted from the data, by reading and analysis circuit 128. The potential diagnoses determined by reading and analysis circuit 128 can then be sent to computer 510 to be reviewed by the user and/or forwarded, or can be immediately forwarded alone or with the supporting raw data to the doctor's office, etc.

Figure 6:
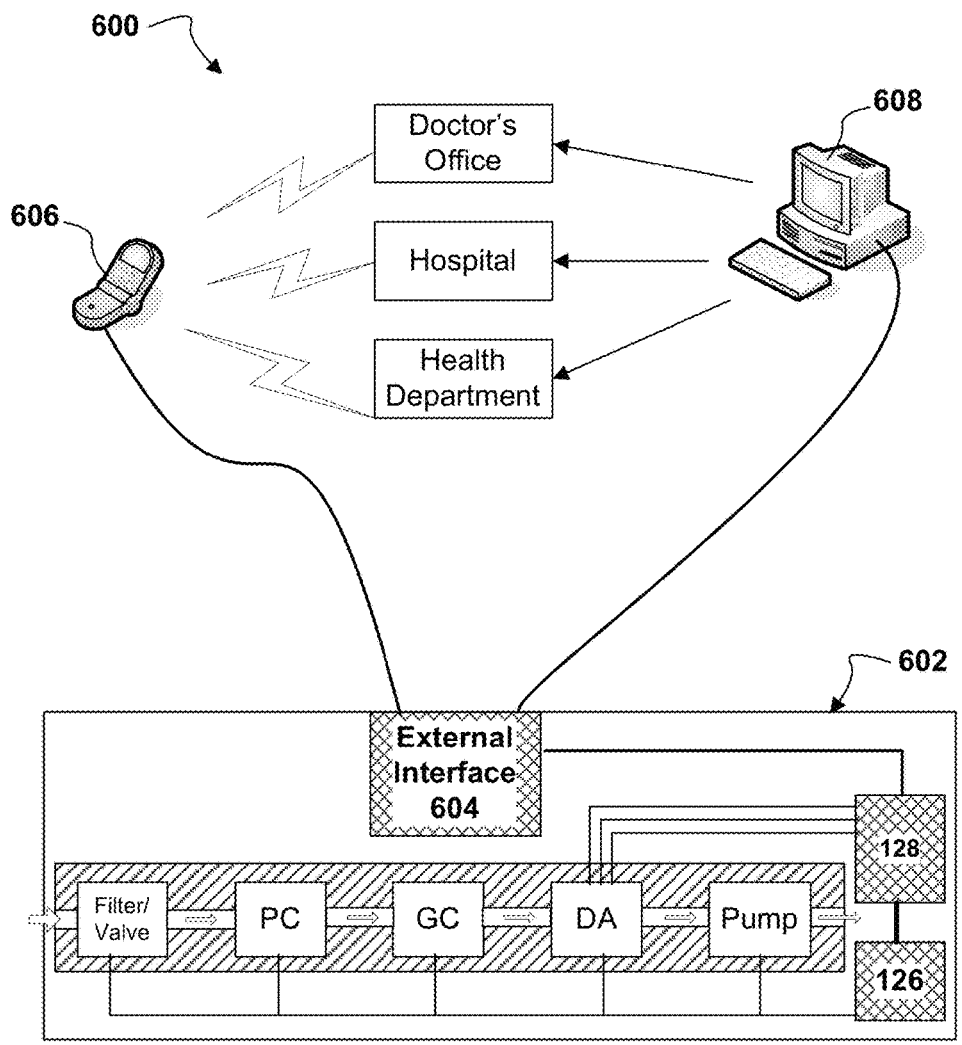
FIG. 6 is a schematic diagram of another alternative embodiment of a gas analysis device and an embodiment of a system using the embodiment of the gas analysis device.

FIG. 6 illustrates an embodiment of a system 600 using an alternative embodiment of a MEMS-based gas analysis device 602. Device 602 is in most respects similar to device 502. The primary difference between device 502 and device 602 is that the wireless transceiver circuit 504 and antenna 506 are replaced with a hardware data interface 604 coupled to reading and analysis circuit 128. In one embodiment, hardware data interface 604 could be a network interface card, but in other embodiments hardware data interface can be an Ethernet card, a simple cable plug, etc. External devices can be connected to device 602 through traditional means such as cables. Although it has a different communication interface, device 602 and system 600 have all the same functionality as device 502 and system 500. As with system 500, in system 600 MEMS-based gas analysis device 602 can transmit data to, and receive data from, one or both of a computer 608 and a wireless device 606, such as a cell phone or personal digital assistant (PDA). When transmitted to wireless device 606 the data can then be forwarded to a doctor's office, hospital, or government health department, and the recipients of the data can in turn send data or instructions back to gas analysis device 602 through the wireless device. As in system 500, when data is transmitted to computer 608 it can be forwarded or can be analyzed by the computer and the result displayed for the user and/or forwarded, and instructions can be transmitted to device 602 through computer 608. Similarly, the data from gas analysis device 602 can be analyzed by reading and analysis circuit 128. After analysis by circuit 128, the extracted information (e.g., one or more diagnoses) and/or the raw data can be forwarded via the hardware data interface 604.

Figure 7:
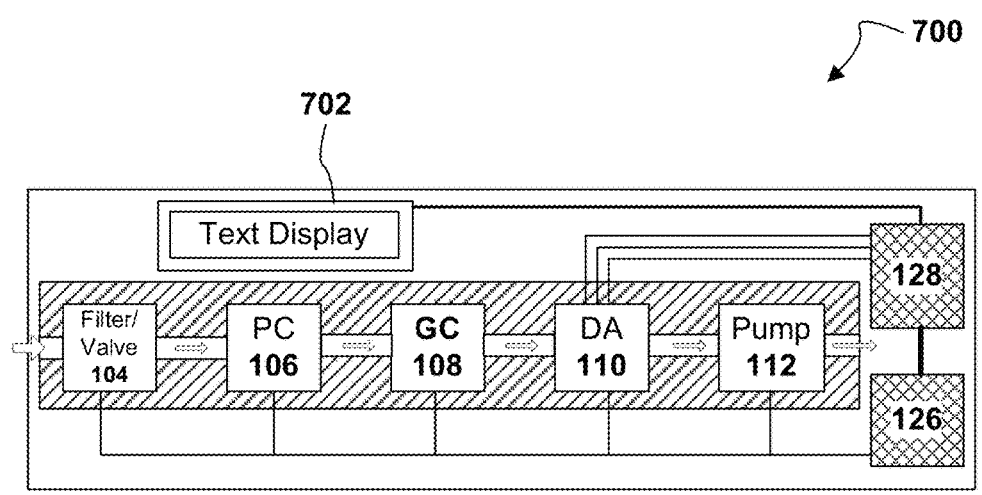
FIG. 7 is a plan-view schematic diagram of an additional alternative embodiment of a gas analysis device.

FIG. 7 illustrates an alternative embodiment of a MEMS-based gas analysis device 700. Device 700 is in most respects similar to device 100. The primary difference between system 700 and device 100 is that device 700 includes an on-board display 702 for conveying to a user the results of the analysis performed by reading and analysis circuit 128.

The illustrated embodiment uses an on-board text display 702, for example an LCD screen that can convey text information to a user. For example, in a health care example display 702 could be used to display the test results in analog numbers indicating the situation of patients. Display 702 could indicate a positive or negative diagnosis, could indicate probabilities of a given diagnosis, or could indicate the raw data from the detector array. In another health care embodiment, simpler displays can be used, such as one with three lights that indicate a positive, negative, or indeterminate result depending on which light is switched on.

Figure 8:
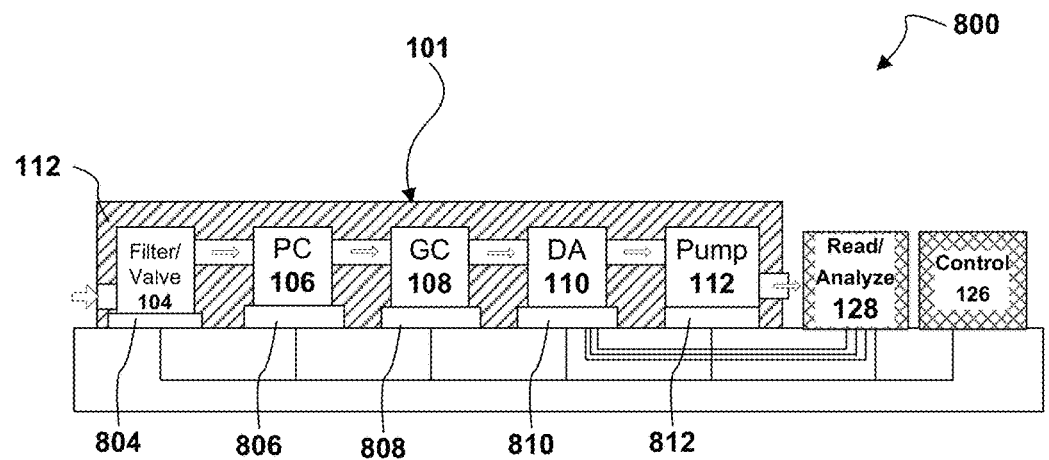
FIG. 8 is a plan-view schematic diagram of an additional alternative embodiment of a gas analysis device.

FIG. 8 illustrates an alternative embodiment of a MEMS-based gas analysis device 800. Device 800 is in most respects similar to device 100. The primary difference between device 800 and device 100 is that in device 800 one or more elements of fluid handling assembly 101 are replaceable. In the illustrated embodiment, the elements are made replaceable by mounting them onto substrate 102 using sockets: filter and valve assembly 104 is mounted to substrate 102 by socket 804, pre-concentrator is mounted to substrate 102 by socket 804, gas chromatograph 108 is mounted to substrate 102 by socket 808, detector array 110 is mounted to substrate 102 by socket 810, and pump 112 is mounted to substrate 102 by socket 812. In one embodiment, sockets 804-812 are sockets such as zero insertion force (ZIF) sockets that permit easy replacement by a user, but in other embodiments other types of sockets can be used. Although the illustrated embodiment shows all the components of fluid handling assembly 101 being replaceable, in other embodiments only some of the components such as pump 112 and detector array 110 can be made replaceable.

Figure 9:
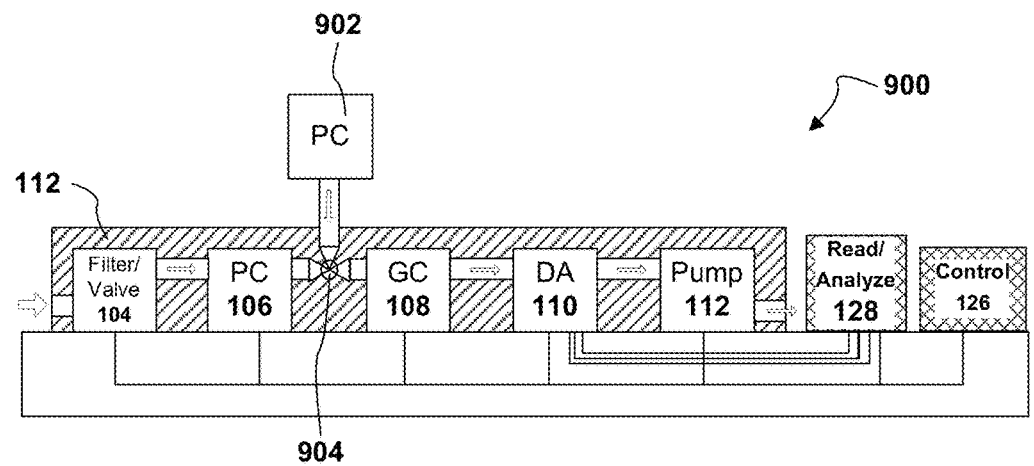
FIG. 9 is a plan-view schematic diagram of an additional alternative embodiment of a gas analysis device.

FIG. 9 illustrates an alternative embodiment of a MEMS-based gas analysis device 900. Gas analysis device 900 is in most respects similar to device 100. The primary difference between device 900 and device 100 is that device 900 includes provisions for an external pre-concentrator 902 (i.e., a pre-concentrator not mounted on substrate 102). In the embodiment shown, a valve 904 is placed between pre-concentrator 106 and gas chromatograph 108, and provisions are made to attach external pre-concentrator 902 to the valve. Valve 904 allows the user to use external pre-concentrator 902 instead of, or in addition to, on-board pre-concentrator 106. In one embodiment external pre-concentrator 902 is a breath collection bag, but in other embodiments it can be something different. In an alternative embodiment of device 900 (not shown), pre-concentrator 106 can be permanently removed and replaced by external pre-concentrator 902. In another embodiment where external pre-concentrator 902 replaces pre-concentrator 106, instead of inserting a valve between pre-concentrator 106 and gas chromatograph 108, external pre-concentrator 902 can be coupled upstream of the filter and valve assembly 104.

FIG. 10 illustrates an embodiment of a gas analysis system 1000 including a front-end pre-concentrator module 1002 coupled to a gas analysis subsystem 1004. Embodiments of system 1000 can be used in place of, or one or more of its components can be used to supplement, filter/valve 104, pre-concentrator 106, gas chromatograph (GC) 108 and detector 110 in gas analysis systems such as the ones shown in FIGS. 1A-1B and 5-9. Similarly, front-end pre concentrator module 1002 can be used in place of, or one or more of its components can be used to supplement, filter/valve 105 and pre-concentrator 106, while gas analysis subsystem 1004 can be used in place of, or one or more of its components can be used to supplement, GC 108 and DA 110.

Front-end pre-concentrator module 1002 includes a filter 1006 coupled to fluid connection 1008 by a switch valve SV1. Fluid connection 1008 is also coupled to the first port of a three-way valve TV1. The second port of three-way valve TV1 is coupled by fluid connection 1010 to the inlet of a trap 1011, and the outlet of trap 1011 is coupled to a fluid connection 1012. The third port of three-way valve TV1 is coupled by fluid connection 1014 to the inlet of a pre-concentrator (PC) 1015, and the outlet of PC 1015 is coupled by fluid connection 1016 to the first port of a second three-way valve TV2. The second port of three-way valve TV2 is coupled by fluid connection 1018 to a second switch valve SV2, and SV2 is in turn coupled by fluid connection 1020 to an inlet of pump P1. An outlet of pump P1 is coupled to fluid connection 1022. The third port of three-way valve TV2 is coupled by fluid connection 1024 to gas analysis subsystem 1004.

In one embodiment of front-end pre-concentrator module 1002, fluid connection 1008 is a temperature-controlled tube that can be heated to a desired temperature so that the moisture and chemicals/VOCs from breath do not condense before reaching PC 1015, but in other embodiments it need not be temperature controlled. In one embodiment, all the fluid connections between the components are made using volatile organic compound (VOC)-free materials that do not absorb or emit VOCs or any contaminants. Teflon is one example of such a material, but in other embodiments other materials are possible.

In one embodiment of pre-concentrator module 1002, all the components are small-scale components, such as micro-scale or micro-electromechanical system (MEMS) components, but in other embodiment the individual components, or any combination of the individual components, need not be small scale. Hence, although the prefix "micro" is used to describe various embodiments or their components, use of the prefix should not be interpreted as any kind of size limitation.

Gas analysis subsystem 1004 includes a gas chromatograph (GC) 1026 whose inlet is coupled to the outlet of front-end pre-concentrator module 1002 by fluid connection 1024. The outlet of GC 1026 is coupled by fluid connection 1028 to the inlet of a detector 1030. The outlet of detector 1030 is coupled to a third switch valve SV3 by fluid connection 1032, and switch valve SV3 can be coupled to further components by fluid connection 1034. For example, in an embodiment where system 1000 is used in the gas analysis systems shown and described for FIGS. 1A-1B and 5-9, or where gas analysis subsystem 1004 is used in such system, fluid connection 1034 can couple switch valve SV3 to a pump and switch valve SV3 can be used to control flow through gas analysis subsystem 1004. In operation, when front-end pre-concentrator module 1002 is operated in release mode (see below), chemicals/VOCs collected in PC 1015 are released due to thermal desorption and carried by the clean air through fluid connection 1024 to gas analysis subsystem 1004. Once in gas analysis subsystem 1004, the chemicals are separated by GC 1026 and directed into detector 1030, where they are sensed.

Front-end pre-concentrator module 1002 has different modes of operation, depending on how the three-way valves and switch valves are configured. Four of these modes are: breath collection mode, dry purge mode, release mode and clean/dry air supply mode. Breath collection mode uses the flow path shown by dotted line ①. As shown in the figure, three-way valves TV1 and TV2 are switched to direct gas containing chemicals/VOCs from filter 1006 through fluid connections 1008 and 1014 and valve TV1 into PC 1015 so that the chemicals/VOCs can be concentrated. Air or moisture that is not collected by PC 1015 is directly exhausted fluid connections 1016-1022, valves TV2 and SV2, and pump P1. To obtain such fast flow rate through the front-end PC, pump P1 can be a fast sampling pump to assist the gas flow so that normal breath into the front-end system is achieved. One or more flow control switch valves are placed in the system, which consistently monitors and adjusts the flow rate during the breath collection. In an alternative embodiment, the pump can be adjusted to maintain the desired flow rate instead of using flow control valve.

Dry purge mode uses flow path shown by dotted line ②. After the breath collection, three-way valve TV1 can be switched to connect front-end PC 1015 with trap 1011. Sampling pump P1 can be used to draw ambient air through trap 1011, which filters all undesired chemicals/VOCs and moisture from the ambient air and results in delivery of clean dry air to PC 1015. The dry air is used to purge PC 1015 to remove moisture trapped by the PC and is exhausted back to ambient through fluid connections 106-1022, valves TV2 and SV2, and pump P. In situations where moisture is not critical to system sensing, the dry purge process may not be needed.

Release mode is used to release chemicals collected in PC 1015 to gas analysis subsystem 1004 and uses flow path shown by dotted line ③. After the breath collection and optional dry purge, the three-way valve TV2 is switched to connect PC 1015 with gas analysis subsystem 1004 through fluid connection 1024. PC 1015 is then heated to desired temperature at its optimum ramping rate so that chemicals/VOCs concentrated by PC 1015 are released due to thermal desorption and carried through fluid connection 1024 to gas analysis subsystem 1004.

Clean/Dry air supply mode uses the flow path shown by the dotted line labeled ④. In addition to direct breath collection, front-end pre-concentrator module 1002 can also be used to produce clean dry air for inhalation right before breath collection from a subject. To provide a dry air supply, three-way valve TV1 is switched to form flow path between the trap and filter 1006. As shown by flow path ④, ambient air is filtered by trap 1011, which removes all undesired chemicals/VOCs from ambient air. Any particles in the air can also be filtered by filter 1006 as well. The resulting clean filtered air can then be inhaled by a test subject so that the background chemicals/VOCs from the environment do not affect or interfere with the subject's exhaled breath.

FIG. 11 illustrates an embodiment of a filter assembly 1100 that can be used as filter 1006 in front-end pre-concentrator module 1002. Filter assembly 1100 includes an inlet 1102, an outlet 1104, and a filter 1006 positioned between the inlet and the outlet to filter raw air entering through inlet 1102 and exhaust filtered air through outlet 1104. In one embodiment, inlet 1102 can be a replaceable mouthpiece that can be disposed of after each breath test to eliminate the risk of disease transmission. In other embodiments, inlet 1102 can be a permanent mouthpiece but the entire filter assembly 1100 can be disposable. Filter 1006 is a filter that can eliminate the breath particles, bacteria, virus from entering the system. In one embodiment, filter 1006 is a High-Efficiency Particulate Arrestor (HEPA) filter, but in other embodiments it can be another type of filter. In still other embodiments, filter 1006 can be a combination of more than one type of filter.

Figure 13A:
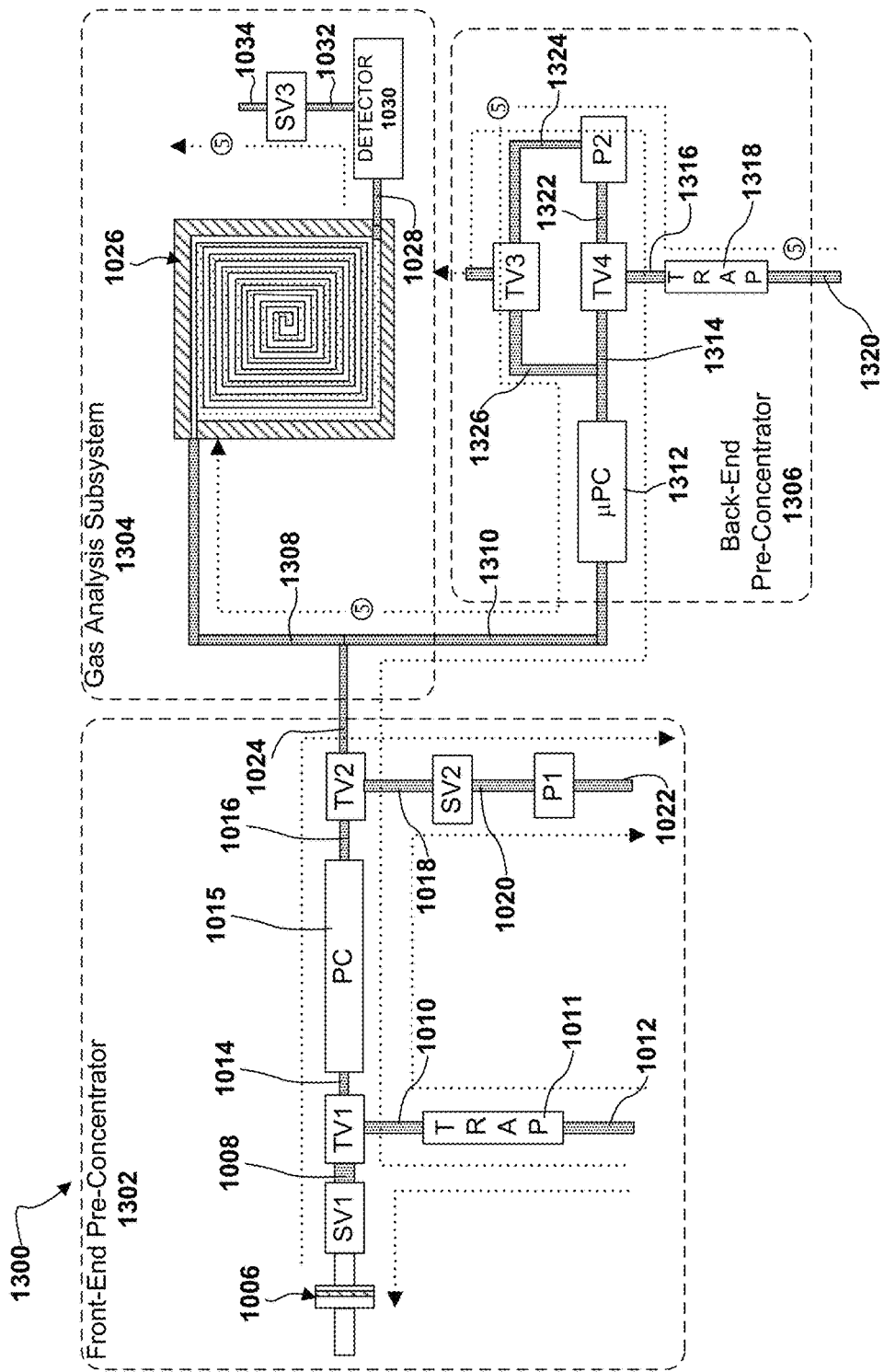
FIG. 13A is a schematic diagram of an embodiment of a gas analysis device including front-end and back-end pre-concentrator modules.
Figure 13B:
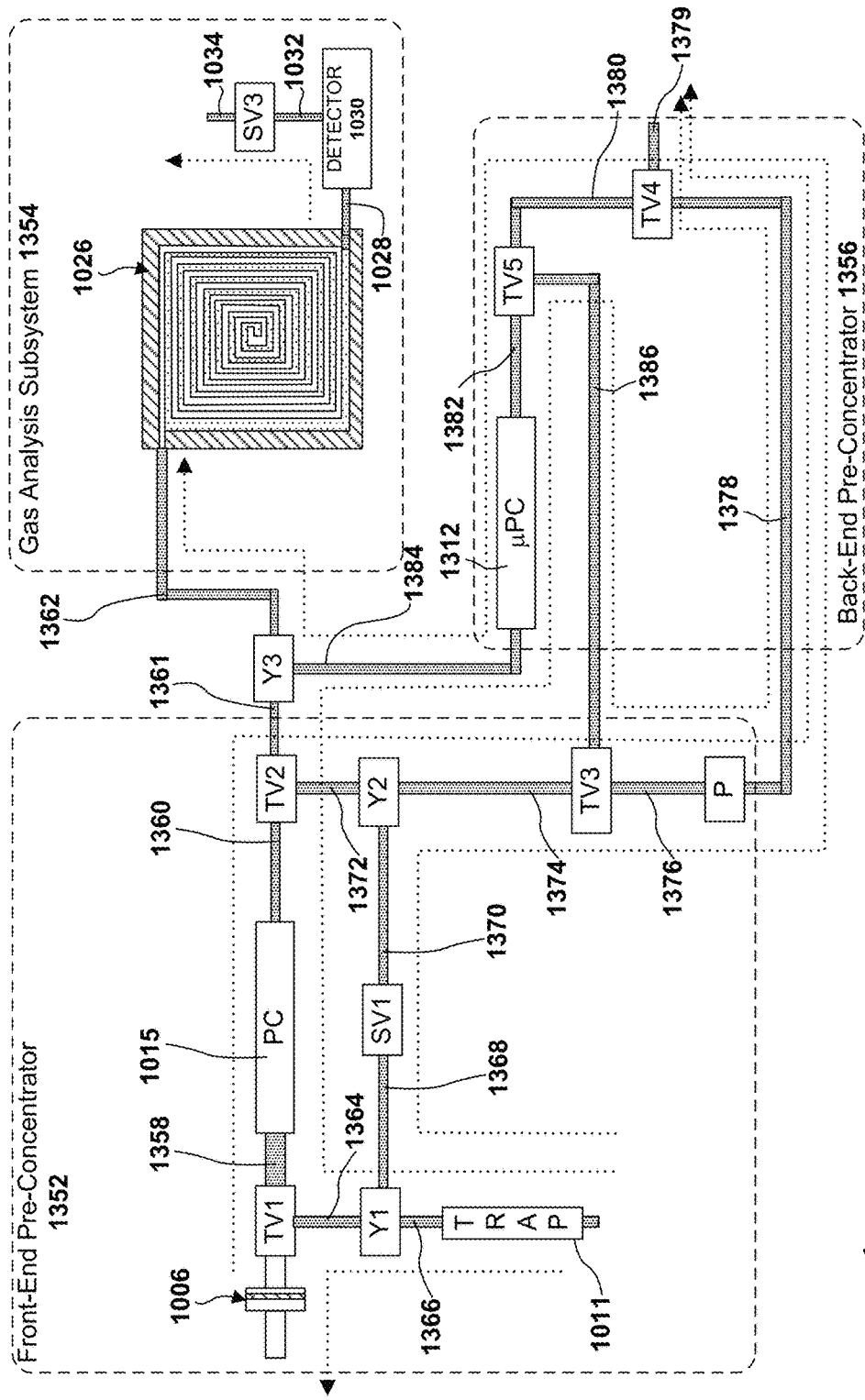
FIG. 13B is a schematic diagram of an alternative embodiment of a gas analysis device including front-end and back-end pre-concentrator modules.
Figure 13C:
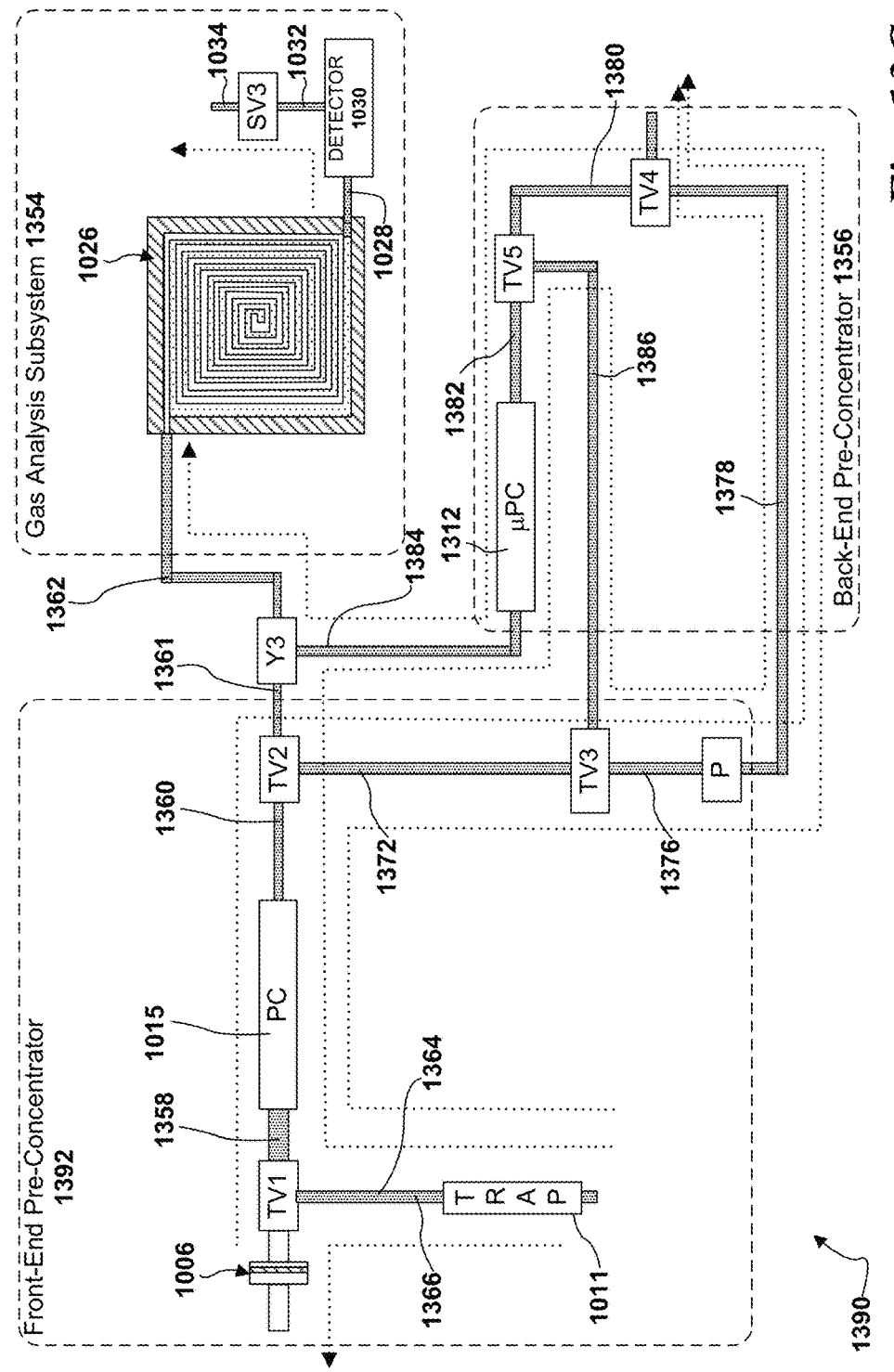
FIG. 13C is a schematic diagram of another alternative embodiment of a gas analysis device including front-end and back-end pre-concentrator modules.
Figure 14:
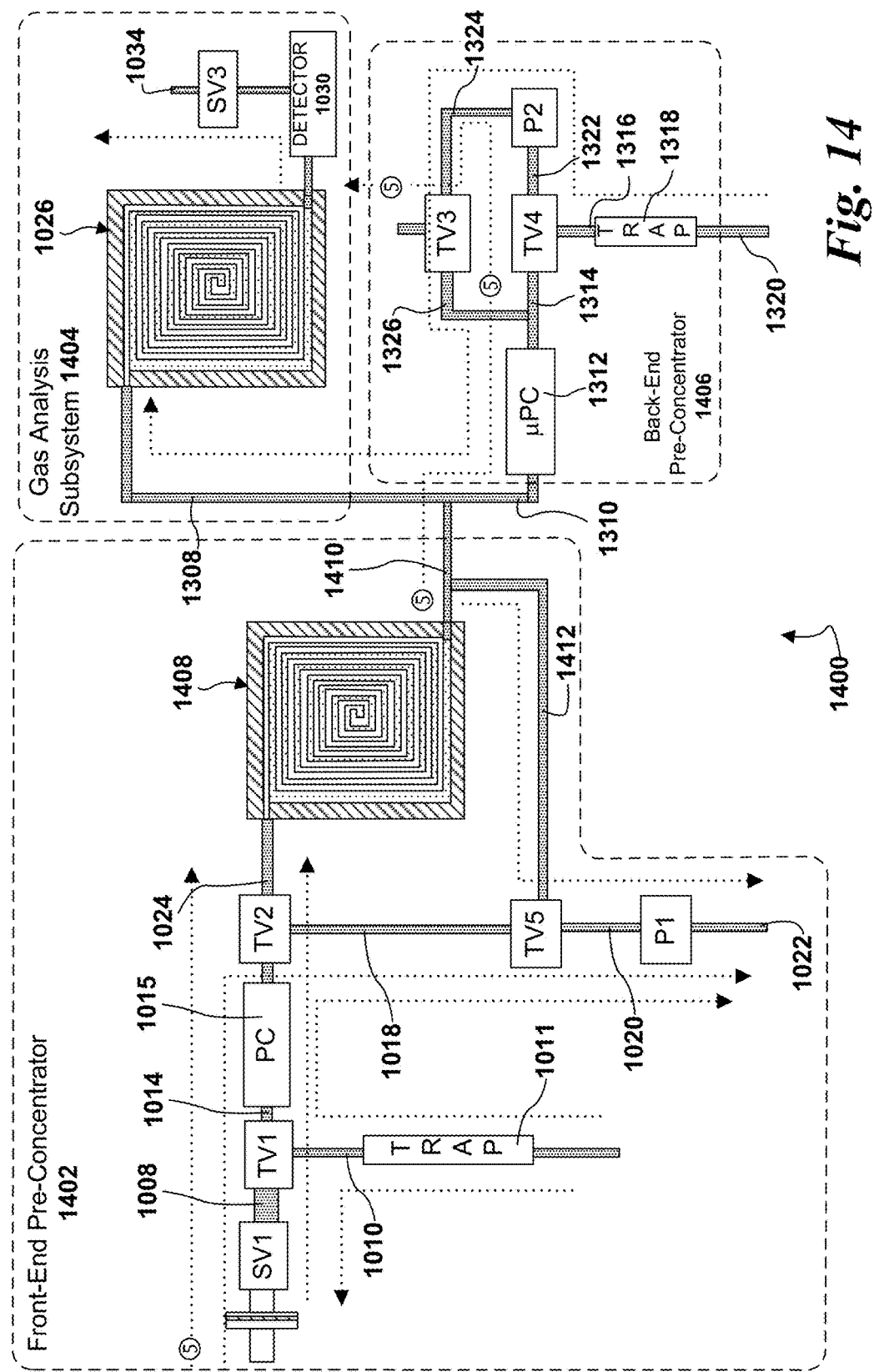
FIG. 14 is a schematic diagram of yet another alternative embodiment of a gas analysis device including front-end and back-end pre-concentrator modules.

FIGS. 12A-12B illustrate embodiments of pre-concentrators that can be used as PC 1015 in front-end pre-concentrator module 1002 or in a back-end pre-concentrator module (see FIGS. 13-14). In one embodiment, PC 1015 is small in size (e.g., <=3 cm) for fast heating and but is also designed to allow a normal breath through flow rate so that a correct breath collection protocol (e.g., 50 cc/sec from breath) can be achieved. To realize such fast flow rates through the PC 1015, pump P1 can be a fast sampling pump that assists the gas flow so that normal breath flow rates into front-end pre-concentrator module 1002 can be achieved.

FIG. 12A illustrate an embodiment of a PC 1200 designed to collect all the chemicals/VOCs of interest from a person's breath or other gas streams. PC 1200 has an inlet 1202, an outlet 1026, and one or more pockets 1204 through which fluid flows and is concentrated. In one embodiment, PC 1200 can have the construction shown and described for FIG. 2A, but in other embodiments it can have the construction shown and described for FIG. 2B or some other construction altogether.

FIG. 12B illustrates an alternative embodiment of a PC 1250. PC 1250 includes an inlet 1252, an outlet 1254 and several parallel micro-PCs 1256a-1256d that extend from the inlet to the outlet. In one embodiment, each micro-PC 1256a-1256d includes one or more pockets 1258 and can have a construction like those shown and described for FIGS. 2A-2B, but in other embodiments can have a different construction. In one embodiment, all parallel micro-PCs 1256a-1256d have the same construction, but in other embodiment the need not all have the same construction. Moreover, each micro-PC can be constructed to concentrate different chemicals/VOCs than the other micro-PCs in PC 1250. The illustrated embodiment of PC 1250 has four parallel micro-PCs, but other embodiments of PC 1250 can have a greater or lesser number of micro-PCs. In operation of PC 1250, during collection a carrier gas containing chemicals enters PC 1250 through inlet 1252, flows simultaneously through pockets in each of the parallel micro-PCs 1256a-1256d where chemicals/VOCs are concentrated for later release. During release, clean air flows through PC 1250 while micro-PCs 1256a-1256d can be heated, one at a time or simultaneously, to release the chemicals concentrated in the pockets of each parallel micro-PC.

FIG. 13A illustrates an alternative embodiment of a gas analysis system 1300. Embodiments of system 1300 can be used in place of, or one or more of its components can be used to supplement, filter/valve 104, pre-concentrator 106, gas chromatograph (GC) 108 and detector 110 in gas analysis systems such as the ones shown in FIGS. 1A-1B and 5-9. Similarly, front-end pre concentrator module 1302 and/or back-end pre-concentrator 1306 can be used in place of, or one or more of its components can be used to supplement, filter/valve 105 and pre-concentrator 106, while gas analysis subsystem 1304 can be used in place of, or one or more of its components can be used to supplement, GC 108 and DA 110.

System 1300 includes a front-end pre-concentrator module 1302 coupled to a gas analysis subsystem 1304 and also coupled to a back-end pre-concentrator module 1306. System 1300 is useful for low-flow concentrated gas analysis. Unlike the existing breath analysis protocol, which requires an on-site breath sample collection in canister or trap and then analysis performed in designated laboratories, the system's front-end breath collection module can retain the collected sample and then release the collected chemicals/VOCs directly to its back-end gas analysis module. Either the miniaturized front-end pre-concentrator module 1302 or back-end module 1306 can be used separately in combination with other chemical/VOC analysis systems.

Fluid connection 1024 couples front-end pre-concentrator module 1302 to both fluid connection 1308 and fluid connection 1310. Fluid connections 1024 and 1308 provide coupling between pre-concentrator module 1302 and gas analysis subsystem 1304, while fluid connections 1024 and 1310 provide coupling between pre-concentrator module 1302 and back-end pre-concentrator 1306. Fluid connections 1024, 1308 and 1310 also provide coupling between gas analysis subsystem 1304 and back-end pre-concentrator 1306.

Front-end pre-concentrator module 1302 has a construction similar to front-end pre-concentrator module 1002 and has four modes of operation similar to those of front-end pre-concentrator module 1002: breath collection mode, shown by flow path ①; dry purge mode, shown by flow path ②; release mode, shown by flow path ③; and dry air supply mode, shown by fluid ④. Within pre-concentrator module 1302, release mode flow path ③ is the same as it is within pre-concentrator module 1002, but in system 1300 flow path ③ differs after leaving pre-concentrator module 1302 because of the presence of back-end pre-concentrator 1306.

Gas analysis subsystem 1304 has a construction similar to gas analysis subsystem 1004, the primary difference being that in gas analysis subsystem 1304 the inlet of GC 1026 is now also coupled via fluid connections 1308 and 1310 to micro-PC 1312 within back-end pre-concentrator 1312.

Back-end pre-concentrator 1306 includes a micro-PC 1312 coupled to fluid connections 1310 and 1314. Fluid connection 1314 is also coupled to the first port of a fourth three-way valve TV4, while the second port of three-way valve TV4 is coupled by fluid connection 1316 to a trap 1318, and trap 1318 is further coupled to the atmosphere by fluid connection 1320. The third port of three-way valve TV4 is coupled to the inlet of pump P2 by fluid connection 1322, and the outlet of pump P2 is coupled by fluid connection 1324 to the third port of third three-way valve TV3. The second port of three-way valve TV3 is vented to atmosphere, while the first port of three-way valve TV3 is coupled by fluid connection 1326 to fluid connection 1314.

Trap 1318 is a trap designed to filter all chemicals/VOCs and moisture from the ambient air to prevent them from contaminating the chemicals/VOCs concentrated in micro-PC 1318, or otherwise affecting the function of gas analysis subsystem 1304. In one embodiment, trap 1318 can be a sorbent trap; sorbent traps are a common approach to produce clean air without moisture or chemicals/VOCs. In other embodiments, however, other types of traps can be used.

Micro-PC 1312 is a pre-concentrator that in some embodiments can have the construction shown in FIG. 12A or 12B, although in other embodiments it can have different constructions. In one embodiment, micro-PC 1312 has a very small size (only about 10 micro liters in volume) so that it can reach a desired temperature in a very short heating time for desorption and analysis and so that it can achieve the highest chemical/VOC concentrations for detection. In one embodiment, a small back-end micro-PC 1312 has a maximum flow rate in range of a few tens milliliter per minute (e.g., 30 ml/min), which does not allow micro-PC 1312 to be used for direct breath collection because it would require too much time to sample the large volumes (4000 ml) needed for breath collection; with a flow rate of 30 ml/min, it could take 30 minutes or more to use micro-PC 1312 to directly collect breath. In an embodiment of front-end PC 1015 sized to have a few milliliters in volume, breath can be sampled within about 20 seconds with flow rate of about 50 ml/sec. The collected chemicals/VOCs are then released by front-end PC 1015 to micro-PC 1312 with a relatively slower flow rate (e.g., 30 ml/min). Since front-end PC 1015 has only a few milliliters in volume, it only required less than 10 seconds for back-end PC 1312 to collect all the VOCs from the front-end PC. The total sampling time to concentrate the breath chemicals/VOCs to back-end PC can be achieved in about 30 seconds with the disclosed embodiments instead of 30 minutes.

Back-end pre-concentrator 1306 has two modes of operation: a collection mode and a release mode. The collection mode of pre-concentrator 1306 operates together with the release mode of pre-concentrator module 1302, hence its flow path is shown by flow path ③, which also corresponds to the flow path of the release mode of pre-concentrator module 1302. With front-end pre-concentrator module 1302 in release mode, gas containing chemicals/VOCs exits PC 1015 can be pulled by pump P2 through fluid connection 1016, three-way valve TV2 and fluid connections 1024 and 1310 into micro-PC 1312, where the chemicals/VOCs are further concentrated. Gas leaving micro-PC 1312 is pulled by pump P2 through three-way valve TV4 and fluid connection 1322, and is exhausted by pump P2 into fluid connection 1324 and three-way valve TV3. Valve TV3 then vents the gases to the atmosphere.

The release mode of back-end pre-concentrator 1306 follows completion of the collection mode. After completion of the collection mode, micro-PC 1312 is heated to a desired temperature at its optimum ramping rate within a few seconds to release the collected chemicals and three-way valves TV2, TV3, and TV4 are switched to allow the air flow shown by flow path ⑤. Pump P2 draws clean air through trap 1318 and three-way valve TV4 and outputs the clean air through fluid connection 1324, three-way valve TV3 and fluid connections 1326 and 1314 into micro-PC 1312. Chemicals and VOCs released by heating micro-PC 1312 are carried by the clean air from micro-PC 1312 to the inlet of GC 1026 through fluid connections 1310 and 1308. GC 1026 then separates the chemicals and outputs them to detector 1030 for detection by detector 1030.

FIG. 13B illustrates another alternative embodiment of a gas analysis system 1350. System 1350 includes a front-end pre-concentrator module 1352 coupled to a gas analysis subsystem 1354 and also coupled to a back-end pre-concentrator module 1356. Like system 1300, system 1350 is useful for low-flow concentrated gas analysis, and either the miniaturized front-end pre-concentrator module 1302 or back-end module 1306 can be used separately in combination with other chemical/VOC analysis systems. Embodiments of system 1350 can be used in place of, or one or more of its components can be used to supplement, filter/valve 104, pre-concentrator 106, gas chromatograph (GC) 108 and detector 110 in gas analysis systems such as the ones shown in FIGS. 1A-1B and 5-9. Similarly, front-end pre concentrator module 1352 and/or back-end pre-concentrator module 1356 can be used in place of, or one or more of its components can be used to supplement, filter/valve 105 and pre-concentrator 106, while gas analysis subsystem 1354 can be used in place of, or one or more of its components can be used to supplement, GC 108 and DA 110.

Front-end pre-concentrator module 1352 includes a filter 1006 coupled the first port of a first three-way valve TV1. As with pre-concentrator module 1302, the filter can be coupled to three-way valve TV1 by a temperature-controlled tube. The second port of three-way valve TV1 is coupled by fluid connection 1364 to a first Y-splitter Y1, and the third port of three-way valve TV1 is coupled by fluid connection 1358 to the inlet of pre-concentrator (PC) 1015. In addition to being coupled to three-way valve TV1, Y-splitter Y1 is coupled by fluid connection 1366 to trap 1011 and by fluid connection 1368 to a first switch valve SV1. The outlet of PC 1015 is coupled by fluid connection 1360 to the first port of a second three-way valve TV2. The second port of three-way valve TV2 is further coupled by fluid connection 1372 to second Y-splitter Y2, and its third port is coupled by fluid connection 1361 to third Y-splitter Y3. Third Y-splitter Y3 is further coupled to the inlet of GC 1026 by fluid connection 1362 and to micro-PC 1312 by fluid connection 1384. Second Y-splitter Y2 is coupled to switch valve SV1 by fluid connection 1370 is also coupled to a first port of third three-way valve TV3 by fluid connection 1374. The second port of three-way valve TV3 is coupled by fluid connection 1386 to a fifth three-way valve TV5 within back-end pre-concentrator 1356, while the third port of three-way valve TV3 is coupled to an inlet of pump P by fluid connection 1376. The outlet of pump P is coupled by fluid connection 1378 to the first port of a fourth three-way valve TV4 in back-end pre-concentrator 1356.

Front-end pre-concentrator module 1352 has four modes of operation: breath collection mode, shown by flow path ①; front-end release mode, shown by flow path ②; back-end release mode, shown by flow path ③; and dry air supply mode, shown by fluid ④. As with other embodiments described herein, flow paths ①-④ can be created by appropriate configuration of the switch valves, three-way valves, and Y-splitters.

Gas analysis subsystem 1354 has a construction similar to gas analysis subsystem 1304, the primary difference being that in gas analysis subsystem 1354 the inlet of GC 1026 is now coupled to front-end pre-concentrator 1352 via Y-splitter Y3 and fluid connections 1361 and 1362, and is coupled to back-end pre-concentrator 1356 via Y-splitter Y3 and fluid connections 1362 and 1384.

Back-end pre-concentrator 1356 includes a micro-PC 1312 coupled to Y-splitter Y3 by fluid connection 1384 and coupled to the third port of fourth three-way valve TV5 by fluid connection 1382. Micro-PC 1312 is similar to micro-PC 1312 described for FIG. 13A and subject to the same variations. The first port of three-way valve TV5 is coupled by fluid connection 1380 to the third port of third three-way valve TV4, while the second port of three-way valve TV5 is coupled by fluid connection 1386 to three-way valve TV3 within the front-end pre-concentrator. The second port of three-way valve TV4 is vented to atmosphere, while the first port of three-way valve TV4 is coupled to the outlet of pump P by fluid connection 1378.

Back-end pre-concentrator 1306 has two modes of operation: a collection mode that operates together with the front-end release mode of front-end pre-concentrator 1352, and a release mode that operates together with the back-end release mode of front-end pre-concentrator 1352. Hence, the collection mode of back-end pre-concentrator 1352 is shown in the figure by flow path ②, which corresponds to the front-end release mode of the front-end pre-concentrator, and the release mode of back-end pre-concentrator 1352 is shown by flow path ③, which corresponds to the back-end release mode of the front-end pre-concentrator. As with other embodiments described herein, flow paths ②-③ can be created by appropriate configuration of the switch valves, three-way valves, and Y-splitters.

With front-end pre-concentrator module 1352 in its front-end release mode, gas containing chemicals/VOCs exits PC 1015 can be pulled by pump P through the fluid connections and components along flow path ② and into micro-PC 1312, where the chemicals/VOCs are further concentrated. Gas leaving micro-PC 1312 follows the remainder of flow path ② until it reaches valve TV4, which vents the gases to the atmosphere. With front-end pre-concentrator 1352 in its back-end release mode, micro-PC 1312 is heated to a desired temperature at its optimum ramping rate within a few seconds to release the collected chemicals. Chemicals and VOCs released by heating micro-PC 1312 are carried along flow path ③ by clean air moved by pump P through the fluid connections and components to the inlet of GC 1026 through fluid connections 1384 and 1362. GC 1026 then separates the chemicals and outputs them to detector 1030 for detection by detector 1030.

FIG. 13C illustrates another alternative embodiment of a gas analysis system 1390. Embodiments of system 1390 can be used in place of, or one or more of its components can be used to supplement, filter/valve 104, pre-concentrator 106, gas chromatograph (GC) 108 and detector 110 in gas analysis systems such as the ones shown in FIGS. 1A-1B and 5-9. Similarly, front-end pre concentrator module 1392 and/or back-end pre-concentrator 1356 can be used in place of, or one or more of its components can be used to supplement, filter/valve 105 and pre-concentrator 106, while gas analysis subsystem 1354 can be used in place of, or one or more of its components can be used to supplement, GC 108 and DA 110.

System 1390 is in most respects similar to system 1350 shown in FIG. 13B. The primary difference is in the front-end pre-concentrator 1392. Pre-concentrator module 1392 differs from pre-concentrator module 1352 in that pre-concentrator 1392 omits Y-splitters Y1 and Y2, switch valve SV1, and fluid connections 1368 and 1370. As a result, fluid connection couples three-way valve TV2 to three-way valve TV3 and fluid connection 1364 coupled three-way valve TV1 to trap 1011. Like front-end pre-concentrator module 1352, front-end pre-concentrator module 1392 has four modes of operation: breath collection mode, shown by flow path ①; front-end release mode, shown by flow path ②; back-end release mode, shown by flow path ③; and dry air supply mode, shown by fluid ④. As with other embodiments described herein, flow paths ①-④ can be created by appropriate configuration of the switch valves, three-way valves, and Y-splitters. Within pre-concentrator 1392, however, flow path ③ is modified so that it flows through valve TV1, PC 1015, and valve TV2 as shown instead of flowing through the removed Y-splitters and the fluid connections and components between them. Outside of pre-concentrator 1392, flow path ③ is substantially the same as it is in pre-concentrator 1352.

FIG. 14 illustrates an alternative embodiment of a gas analysis system 1400 that can be used in situations where moisture is not desired or allowed in the back-end gas analysis system. When the dry purge cannot completely eliminate the moisture in front-end PC, or when complete moisture removal reduces the amount of chemicals/VOCs collected by the front-end PC, an additional moisture extraction from the front-end PC without affecting the amount of collected VOCs can be used. Embodiments of system 1400 can be used in place of, or one or more of its components can be used to supplement, filter/valve 104, pre-concentrator 106, gas chromatograph (GC) 108 and detector 110 in gas analysis systems such as the ones shown in FIGS. 1A-1B and 5-9. Similarly, front-end pre concentrator module 1402 can be used in place of, or one or more of its components can be used to supplement, filter/valve 105 and pre-concentrator 106, while gas analysis subsystem 1404 can be used in place of, or one or more of its components can be used to supplement, GC 108 and DA 110.

System 1400 includes a front-end pre-concentrator module 1402 coupled to a gas analysis subsystem 1404 and also coupled to a back-end pre-concentrator 1406. Gas analysis subsystem 1404 is similar to gas analysis subsystems 1004 and 1304 and back-end pre-concentrator 1406 is similar to back-end pre-concentrator 1306. Front-end pre-concentrator module 1402 is configured similarly to pre-concentrator modules 1002 and 1302, the principal differences in pre-concentrator module 1402 being the addition of a gas chromatograph (GC) 1408 and the replacement second switch valve SV2 with a fifth three-way valve TV5. Three-way valve TV5 is has its first port coupled to the second port of second three-way valve TV2 and has its third port coupled to pump P1 by fluid connection 1020. GC 1408 has its inlet coupled to fluid connection 1024 and its outlet coupled to the second port of three-way valve TV5 by fluid connections 1410 and 1412. Fluid connection 1410 also couples pre-concentrator module 1402 to gas analysis subsystem 1404 and back-end pre-concentrator 1406. Fluid connections 1410 and 1308 provide coupling between additional GC 1408 and GC 1026, while fluid connections 1410 and 1310 provide coupling between additional GC 1408 and back-end pre-concentrator 1306. Fluid connections 1410, 1308 and 1310 also provide a coupling between GC 1026 and back-end pre-concentrator 1406.

Pre-concentrator module 1402 has five modes of operation. Three of these modes are similar to those of front-end pre-concentrator module 1002 and 1302: breath collection mode, shown by flow path ①; dry purge mode, shown by flow path ②; and dry air supply mode, shown by flow path ④. The release mode of pre-concentrator module 1402, shown by flow path ③, is similar to the release flow path ③ of pre-concentrator modules 1002 and 1302, the primary difference being that in pre-concentrator module 1402 flow path ③ travels from fluid connection 1024 into GC 1408 and exits GC 1408 through fluid connection 1410. After leaving GC 1408, flow path ③ carries the flow into and through back-end pre-concentrator 1406 in a manner similar to that shown for back-end pre-concentrator 1306.

Pre-concentrator 1402 also includes a secondary dry-purge mode, shown by flow path ⑤, that can be used to reduce moisture in PC 1015 if the dry-purge shown by flow path ② does not succeed in extracting enough moisture. Because the secondary dry purge used GC 1408, it can be used to remove moisture from PC 1015 without losing any chemicals/VOCs collected in PC 1015. In some situations, the secondary dry purge may not be needed and a direct moisture separation process may be applied directly.

During the secondary dry-purge mode, three-way valves TV1 and TV5 are switched to produce the flow path through trap 1011, front-end PC 1015, GC 1408, and then exhaustion to ambient. PC 1015 is heated to release chemicals/VOCs as well remaining moisture within the PC. As the release VOCs and moisture entering GC 1408, moisture will pass thought the GC and be exhausted to ambient first as shown in FIG. 9. Three-way valves TV3, TV4, and TV5 are then switched promptly so that remaining chemicals/VOCs follow flow path ③ and are channeled and collected by the back-end micro-PC. As a result, no moisture enters or is collected by micro-PC 1312. Once chemicals/VOCs are collected in micro-PC 1312, three-way valves TV3 and TV4 can be switched so that back-end pre-concentrator 1406 enters its own release mode, shown by flow path ⑥. Flow path ⑥ in system 1400 is similar to flow path ⑤ in system 1300, in that it carries chemicals/VOCs from back-end pre-concentrator 1406 into gas analysis subsystem 1404.

In one embodiment, the front-end PC 1015 can be pulseheated periodically to different temperatures and durations in synchronization with switching the three-way valves to conditionally release different chemicals/VOCs or moisture to control flow of the desired chemicals/VOCs to back-end micro-PC 1312 (flow path ③) or undesired chemicals/VOCs or moisture to ambient exhaust (flow path ⑤). Chemicals/VOCs collected by the back-end micro-PC 1312 are then released and analyzed by gas analysis subsystem 1404 (flow path ⑥).

Figure 15:
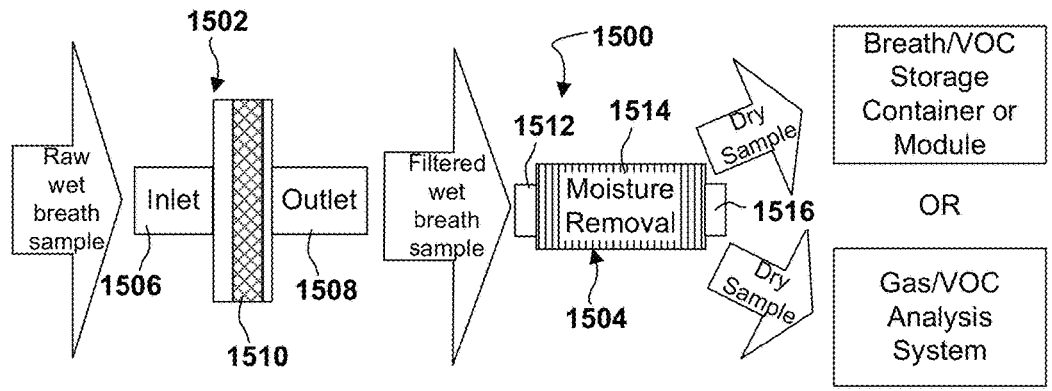
FIG. 15 is a schematic diagram of an embodiment of a disposable filter assembly.

FIG. 15 illustrates an embodiment of a filter assembly 1500. Filter assembly 1500 can be coupled to a breath/gas/chemical storage container or external pre-concentrator, such as pre-concentrator/breath collection bag 902 shown in FIG. 9. Alternatively, combined dry filter assembly and moisture removal compartment can be coupled directly to a gas analysis system. For example, in the gas analysis systems shown in FIGS. 1A-1B and 5-9 the combined dry filter assembly and moisture removal compartment can be part of filter/valve 104 or in the gas analysis system of FIG. 10, 13 or 14, the combined dry filter assembly and moisture removal compartment can be part of filter/valve 104 can replace or supplement filter 1006.

Filter assembly 1500 includes a dry filter assembly 1502 coupled to a moisture removal module 1504. In this embodiment, the moisture removal module can be a small standalone adaptor compartment that bridges between dry filter assembly 1502 and the breath collection container or gas analysis system to which filter assembly 1500 is coupled. As the exhaled breath is first filtered by the dry filter assembly 1502 for particulates, microbacteria and/or viruses, the air still contains high humidity (>90%). When the air continues passing through the moisture removal compartment, the water vapor is further filtered by the salt compound contained in the compartment. The final dry exhaled air is then collected by the container or directly analyzed by the system.

Dry filter assembly 1502 includes an inlet 1506, an outlet 1508 and a dry filter 1510 positioned between the inlet and the outlet. In one embodiment, dry filter 1510 can be a HEPA filter, but in other embodiments dry filter 1510 can be another type of filter or a combination of different types of filters. In one embodiment, inlet 1506 can be a disposable mouthpiece through which a patient can breathe into the filter assembly, while in other embodiments the entire dry filter assembly 1502 can be disposable. In still other embodiments, the entire filter 1500, including dry filter assembly 1502 and the moisture removal compartment 1504, can be disposable.

Moisture removal module 1504 includes an inlet 1512, a moisture removal compartment 1514, and an outlet 1516. In one embodiment, moisture removal compartment 1514 is packed with compounds with a high affinity for molecular water, such as small amounts of a salt compound that can absorb significant amount of water and can be used to effectively absorb moisture directly from exhaled breath. Examples of salt compounds that can be used include lithium chloride (LiCl), lithium bromide (LiBr), lithium iodide (LiI) and sodium bromide (NaBr). In other embodiments other compounds, such as non-ionic salt compounds, can be used. In one embodiment the compound can be in powder form, but in other embodiments it can be in granular form, in porous solid form, or in some other form. In still other embodiments, the compound be coated on a porous substrate, and the coated porous substrate is then packed into the moisture removal compartment. In one embodiment, the porous substrate can be a gas-permeable media/membrane such as glass wool, but in other embodiments other types of porous substrates can be used. The amount of compound to be used depends on the amount of sampling air and the number of iterations before it needs to be replaced or refreshed; in some embodiments only a few grams are needed for 1 L of air sampling. When the humid air flows through the compartment, the salt compound will strongly attract the water vapor due to its strong water affinity. As a result, the air that passes through the disclosed moisture removal compartment will result in a moisture free or low moisture sample at its output.

Figure 16:
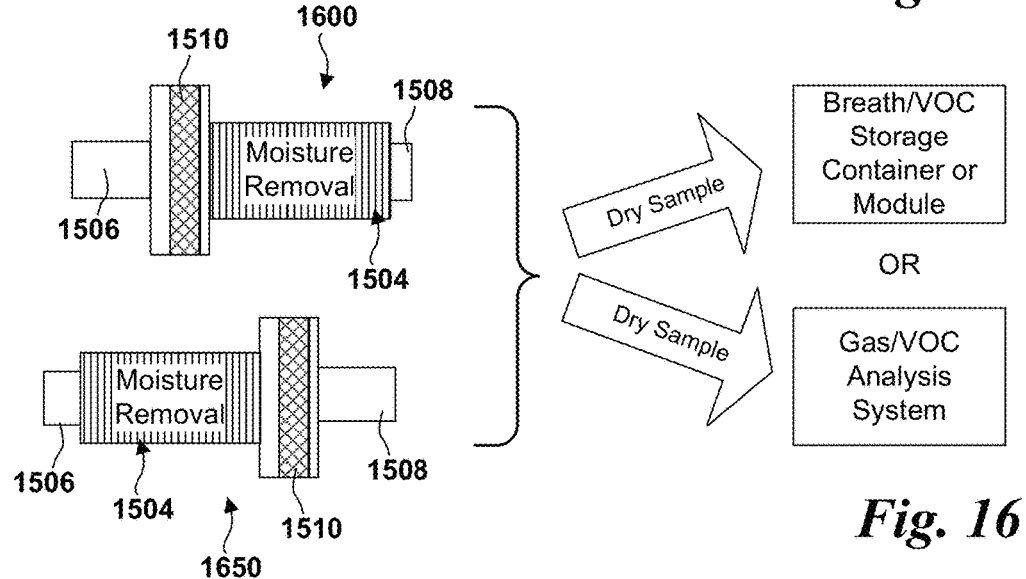
FIG. 16 is a schematic diagram of a pair of alternative embodiments of a filter assembly.

FIG. 16 illustrate a pair of alternative embodiments 1600 and 1650 of a filter assembly. Filter assemblies 1600 and 1650 include substantially the same components as filter assembly 1500, but in filter assembly 1600 moisture removal compartment 1514 is integrated into outlet 1508 of dry filter assembly 1502. In filter assembly 1650, moisture removal compartment 1514 is instead integrated into inlet 1506 if dry filter assembly 1502.

Figure 17A:
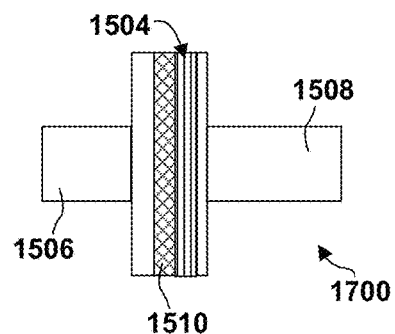
FIG. 17A-17B are schematic diagrams of additional alternative embodiments of a disposable filter assembly.
Figure 17B:
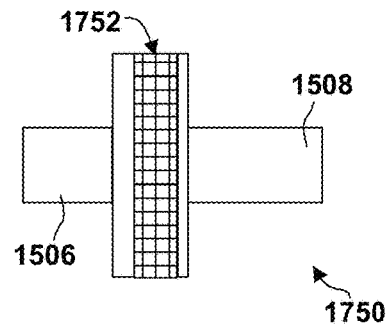

FIGS. 17A-17B illustrate further embodiments of filters 1700 and 1750 that integrate the dry filter with the moisture removal compartment in the same assembly. In filter assembly 1700, moisture removal compartment 1514 is integrated into the main body of dry filter 1502, so that it is in downstream of dry filter 1510. In other embodiments, moisture removal compartment 1514 can be positioned upstream of dry filter 1510. In filter 1750, dry filtering and moisture removal are combined in a single filter 1752 that can be positioned in a filter assembly between inlet 1506 and outlet 1508. Filter 1752 can be formed by coating water-absorbing compounds, which can be at least any of the compounds mentioned above for moisture removal compartment 1514, directly on a porous substrate. In one embodiment the porous substrate can be glass wool, but in others it can be some other type of porous filter or gas-permeable membrane that provides a large surface area of the coated compound to the air flow. It can effectively prevent passage of moisture through the treated filter, thus achieving dry filtration and moisture removal in a single filter.

Figure 18:
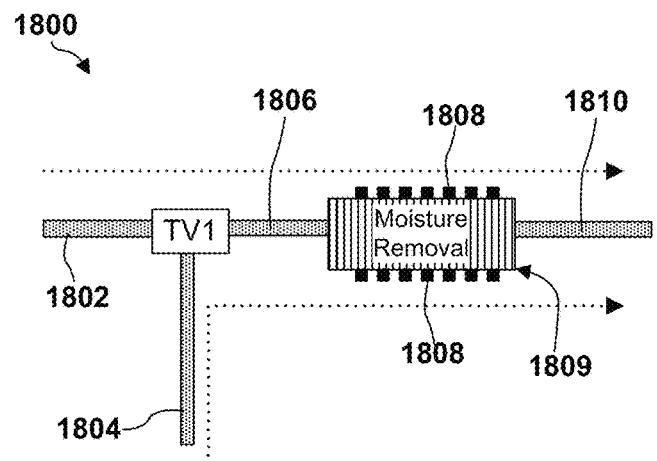
FIG. 18 is a schematic diagram of an embodiment of a re-usable moisture-removal assembly.

FIG. 18 illustrates an embodiment of a re-usable moisture removal assembly 1800 that can be either couple to or integrated within a gas analysis system or used as an external apparatus. For example, in embodiments of the gas analysis systems shown in FIGS. 1A-1B and 5-9 the moisture removal assembly can be part of filter/valve 104 or could be positioned upstream or downstream of filter/valve 104. In the gas analysis system of FIG. 10, 13 or 14, moisture removal assembly 1800 can replace or supplement filter 1006. The reusability of such miniaturized moisture removal assembly is especially beneficial for a portable gas analysis system for environment monitoring, where many iterations of humid gas sampling may be needed without usage of disposable parts.

Assembly 1800 includes a three-way valve TV1 having a humid air inlet 1802 coupled to its first port, a dry air inlet 1804 coupled to its second port, and a fluid connection 1806 coupled between its third port and an inlet of moisture removal compartment 1809. Moisture removal compartment 1809 is similar to compartment 1514 and subject to the same variations. A fluid connection 1810 is coupled to the outlet of the moisture removal compartment 1809. The absorption and desorption of water by salt compound is usually reversible. Molecular water can be driven away from salt compound by heat treatment, similar to sodium chloride formation from salt water. Hence, a heater 1808 is coupled to moisture removal compartment 1809. In one embodiment, heater 1808 can be a separate heater unit, but in other embodiments heater 1808 can be integrally formed with moisture removal compartment 1809. In still other embodiments, heat can be applied to moisture removal compartment 1809 in some other way.

In operation, moisture removal assembly 1800 has two modes: removal mode and disposal mode. During removal mode, three-way valve TV1 is set to allow fluid to flow through humid air inlet 1802, fluid connection 1806, moisture removal compartment 1809 and outlet fluid connection 1810, as shown by flow path ① in the figure. During disposal mode, three-way valve TV1 is set to allow fluid to flow through dry air inlet 1804, fluid connection 1806, moisture removal compartment 1809 and outlet 1810, as shown by flow path ② in the figure. As dry air flows through the system, heater 1808 is activated to heat moisture removal compartment 1809 so that water captured in the compartment is released and carried away through outlet 1810.

Figure 19:
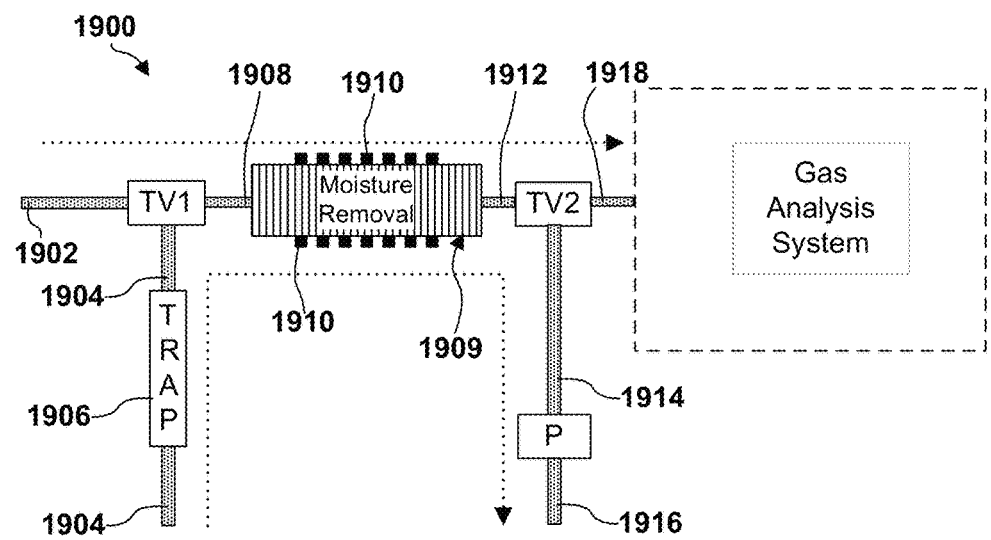
FIG. 19 is a schematic diagram of an alternative embodiment of a re-usable moisture-removal assembly.

FIG. 19 illustrates an alternative embodiment of a reusable moisture removal assembly 1900 that can be either integrated within a gas analysis system or used as an external apparatus. Assembly 1900 includes a first three-way valve TV1 having a humid air inlet 1902 coupled to its first port, a dry air inlet 1904 with a trap 1906 coupled to its second port, and a fluid connection 1908 coupled between its third port and an inlet of moisture removal compartment 1909. Trap 1902 can be a sorbent trap used to filter all chemicals/VOCs and moisture from the ambient air if the dry air entering through inlet 1804 is directly from the environment. A sorbent trap is a common approach to produce clean air, but it cannot selectively remove moisture without also blocking VOCs like the disclosed embodiments using salt compound. Moisture removal compartment 1909 is similar to compartment 1514 and subject to the same variations.

A heater 1910 is coupled to moisture removal compartment 1909. In one embodiment, heater 1910 can be a separate heater unit, but in other embodiments heater 1910 can be integrally formed with moisture removal compartment 1909. In still other embodiments, heat can be applied to moisture removal compartment 1909 in some other way. A fluid connection 1912 is coupled from the outlet of the moisture removal compartment 1909 to the first port of a second three-way valve TV2. The second port of three-way valve TV2 is coupled to an inlet of pump P by fluid connection 1914, and the outlet of pump P is coupled to a fluid connection 1916. The third port of three-way valve TV2 is coupled to a fluid connection 1918, which can then be coupled to whatever device assembly 1900 is used with.

In operation, moisture removal assembly 1900 has two modes of operation: removal mode and disposal mode. During sampling mode, three-way valves TV1 and TV2 are set to allow fluid to flow through humid air inlet 1902, fluid connection 1908, moisture removal compartment 1909, fluid connection 1912, three-way valve TV2 and fluid connection 1918, as shown by flow path ① in the figure. During disposal mode, three-way valves TV1 and TV2 are set to allow fluid to flow through dry air inlet 1904, trap 1906, fluid connection 1908, moisture removal compartment 1909, outlet 1912, three-way valve TV2 and outlet 1914, as shown by flow path ② in the figure. Pump P can be used to produce a fluid flow for flushing out the system. As dry air flows through the system, heater 1910 is activated to heat moisture removal compartment 1909 so that water captured in the compartment is released and carried away through outlet 1916. After the moisture removal compartment is refreshed, the apparatus can then be used again in sampling mode until the compartment is saturated with water, at which point the assembly is put through another disposal cycle.

Device Applications

Pre-clinical studies on human breath analysis have found that certain volatile organic compounds (VOCs) of exhaled human breath are correlated to certain diseases, such as pneumonia, pulmonary tuberculosis (TB), asthma, lung cancer, liver diseases, kidney diseases, etc. The correlations are especially evidential for lung-related diseases. Current analytical systems still rely on large and expensive laboratory instruments, such as gas chromatography (GC) and mass spectrometry (MS). Mass spectrometers in particular are impossible to miniaturize, making widespread use of these diagnostic instruments impossible.

The embodiments of MEMS-based gas analysis sensors discussed above provide a solution to this problem, and in particular could be used advantageously to diagnose and monitor various diseases such as asthma, lung cancer, lung-related diseases, and other non-lung diseases such as kidney and liver diseases, and etc.

Asthma

Asthma is a chronic disease; therefore, regularly monitoring patient's status is helpful to doctor on tracking patient's healing progresses. Therefore, the new idea of handheld diagnostics would make the breath analysis possible done at home or anywhere. In current diagnostics the basic measurement is peak flow rate and the following diagnostic criteria are used by the British Thoracic Society, but the peak flow rate is a physical quantity measurement. Breath analysis could provide specific root causes of the bronchi contraction by measuring the VOCs from patient's breath. Embodiments of the MEMS-based gas analysis systems could be used to monitor the efficacy of the medication. Furthermore, the medication therapy can be tailored to individual patient through this active monitoring by using this home-based device.

Tuberculosis

One third of the world's current population has been infected by TB. And 75% of the cases are pulmonary TB. The infected rate in the developing countries is much higher than developed countries. Therefore, there are urgent needs of developing affordable diagnostic devices for developing countries. Embodiments of the MEMS-based gas analysis system would provide a cost-effective solution. Tuberculosis is caused by *Mycobacterium*. Current diagnostic is time consuming and difficult since culturing the slow growing *Mycobacterium* takes about 6 weeks. Therefore, a complete medical evaluation, including chest X-ray, Tuberculosis radiology, tuberculin skin test, microbiological smears and cultures, is used to get more accurate assessment. Therefore, the rapid diagnostic is very valuable and our breath analysis approach could achieve such needs.

Lung Cancer

With early detection and treatment, the 5-year survival rate for lung cancer improves dramatically. Current diagnostic methods, such as chest X-ray and CT (computed tomography) scan, are difficult to detect early stage lung cancer. Breath analysis using embodiments of the MEMS-based gas analysis system could diagnose the early stage lung cancer.

Classification of Lung-Related Diseases with Similar Symptoms

Breath analysis on exhaled VOCs is viable method to identify patient's lung-related diseases, which has similar symptoms. For example, embodiments of the MEMS-based gas analysis system can provide the tested data to medical doctors to classify which disease between cool, lung-cancer, or pneumonia the patient would have. Breath analysis would be the first screening test because of its simplicity before going for more tedious diagnostic measurements.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. An apparatus comprising:
a front-end pre-concentrator module including an inlet, an outlet, and at least one valve to control flow through the inlet, the outlet, or both, the front-end pre-concentrator module comprising:
a pre-concentrator having an inlet and an outlet,
a first three-way valve coupled to the inlet of the pre-concentrator and a second three-way valve coupled to the outlet of the pre-concentrator,
a trap coupled to the first three way valve,
a switch valve coupled to the second three-way valve, and
a pump coupled to the switch valve;
a back-end pre-concentrator module including an inlet, an outlet, and at least one valve to control flow through the inlet, the outlet, or both; and
a gas analysis module having an inlet and an outlet and including a gas chromatograph having an inlet and an outlet, wherein the outlet of the front-end pre-concentrator and the outlet of the back-end pre-concentrator are coupled to the inlet of the gas analysis module.

2. The apparatus of claim 1 wherein the front-end pre-concentrator module further comprises a filter coupled to the first three-way valve.

3. The apparatus of claim 2 wherein the front-end pre-concentrator module further comprises a switch valve coupled between the filter and the first three-way valve.

4. The apparatus of claim 1 wherein the back-end pre-concentrator module comprises:
a pre-concentrator having an inlet and an outlet, the inlet being coupled to the second three-way valve and to the inlet of the gas chromatograph;
a fourth three-way valve coupled to the outlet of the pre-concentrator;
a trap coupled to the fourth three-way valve;
a second pump coupled to the fourth three-way valve; and
a third three-way valve coupled to the second pump and coupled to a fluid connection between the outlet of the pre-concentrator and the fourth three-way valve.

5. The apparatus of claim 4 wherein the back-end pre-concentrator module further comprises a vent coupled to the third three-way valve.

6. The apparatus of claim 1 wherein the gas analysis module further comprises a detector coupled to the outlet of the gas chromatograph.

7. The apparatus of claim 1 wherein the gas analysis module further comprises:
a detector coupled to the outlet of the gas chromatograph;
a control circuit coupled to the gas chromatograph and to the detector, wherein the control circuit can communicate with the gas chromatograph and to the detector;
a readout circuit coupled to the detector and to the control circuit, wherein the readout circuit can communicate with the control circuit and the detector; and
a communication interface coupled to the readout circuit.

8. The apparatus of claim 7 wherein the readout circuit includes an analysis circuit and associated logic to analyze the output signals received from the detector.

9. An apparatus comprising:
a front-end pre-concentrator module including an inlet, an outlet, and at least one valve to control flow through the inlet, the outlet, or both, the front-end pre-concentrator module comprising:
a pre-concentrator having an inlet and an outlet, a first three-way valve coupled to the inlet of the pre-concentrator and a second three-way valve coupled to the outlet of the pre-concentrator, a trap coupled to the first three way valve, a third three-way valve coupled to the second three-way valve, and a pump coupled to the third three-way valve;

a back-end pre-concentrator module including an inlet, an outlet, and at least one valve to control flow through the inlet, the outlet, or both; and a gas analysis module having an inlet and an outlet and including a gas chromatograph having an inlet and an outlet, wherein the outlet of the front-end pre-concentrator and the outlet of the back-end pre-concentrator are coupled to the inlet of the gas analysis module.

10. The apparatus of claim 9 wherein the front-end pre-concentrator module further comprises:
a first Y-splitter coupled between the first three way valve and the trap;
a second Y-splitter coupled between the second three-way valve and the third three-way valve; and
a fluid connection between the first Y-splitter and the second Y-splitter.

11. The apparatus of claim 10, further comprising a switch valve coupled between the first Y-splitter and the second Y-splitter.

12. The apparatus of claim 9 wherein the front-end pre-concentrator module further comprises a filter coupled to the first three-way valve.

13. The apparatus of claim 12 wherein the filter is coupled to the first three-way valve by a temperature-controlled tube.

14. The apparatus of claim 9 wherein the inlet of the gas chromatograph is coupled to the second three-way valve by a third Y-splitter.

15. The apparatus of claim 14 wherein the back-end pre-concentrator module comprises:
a pre-concentrator coupled to the third Y-splitter;
a fourth three-way valve coupled to the pump and to a vent; and
a fifth three-way valve coupled to the pre-concentrator, the third three-way valve and the fourth three-way valve.

16. An apparatus comprising:
a front-end pre-concentrator module including an inlet, an outlet, and at least one valve to control flow through the inlet, the outlet, or both, the front-end pre-concentrator module comprising:
a pre-concentrator having an inlet and an outlet,
a first three-way valve coupled to the inlet of the pre-concentrator and a second three-way valve coupled to the outlet of the pre-concentrator,
a trap coupled to the first three way valve,
a fifth three-way valve coupled to the second three-way valve and to a first pump, and
an additional gas chromatograph having:
an inlet coupled to the second three-way valve, and
an outlet coupled to the inlet of the gas chromatograph, to the inlet of the back-end pre-concentrator, and to the fifth three-way valve;
a back-end pre-concentrator module including an inlet, an outlet, and at least one valve to control flow through the inlet, the outlet, or both; and
a gas analysis module having an inlet and an outlet and including a gas chromatograph having an inlet and an outlet, wherein the outlet of the front-end pre-concentrator and the outlet of the back-end pre-concentrator are coupled to the inlet of the gas analysis module.

17. The apparatus of claim 16 wherein the front-end pre-concentrator module further comprises a filter coupled to the first three-way valve.

18. The apparatus of claim 17 wherein the filter and the first three-way valve are coupled by a temperature-controlled tube.

19. The apparatus of claim 16 wherein the front-end pre-concentrator module further comprises a switch valve coupled between the filter and the first three-way valve.

20. The apparatus of claim 16 wherein the back-end pre-concentrator module comprises:
a pre-concentrator having an inlet and an outlet, the inlet being coupled to the inlet of the gas chromatograph and the outlet of the additional gas chromatograph;
a fourth three-way valve coupled to the outlet of the pre-concentrator;
a trap coupled to the fourth three-way valve;
a second pump coupled to the fourth three-way valve;
a third three-way valve coupled to the second pump and coupled to a fluid connection between the pre-concentrator and the fourth three-way valve.

21. The apparatus of claim 20 wherein the back-end pre-concentrator module further comprises a vent coupled to the third three-way valve.

22. A process comprising:
providing an apparatus including:
a front-end pre-concentrator module including an inlet, an outlet, and at least one valve to control flow through the inlet, the outlet, or both, the front-end pre-concentrator module including:
a pre-concentrator having an inlet and an outlet,
a first three-way valve coupled to the inlet of the pre-concentrator and a second three-way valve coupled to the outlet of the pre-concentrator,
a trap coupled to the first three way valve,
a second switch valve coupled to the second three-way valve, and
a pump coupled to the second switch valve;
a back-end pre-concentrator module including an inlet, an outlet, and at least one valve to control flow through the inlet, the outlet, or both; and
a gas analysis module having an inlet and an outlet and including a gas chromatograph having an inlet and an outlet, wherein the outlet of the front-end pre-concentrator and the outlet of the back-end pre-concentrator are coupled to the inlet of the gas analysis module;
configuring the at least one valve in the front-end pre-concentrator and the at least one valve in the back-end pre-concentrator to form a flow path to receive a gas sample through the front-end pre-concentrator, concentrate chemicals or volatile organic compounds carried by the gas and direct them to the gas analysis module, the back-end pre-concentrator module, or both; and
configuring the first and second three-way valves to form a flow path to receive a gas sample through the first three-way valve and concentrate chemicals or volatile organic compounds carried by the gas in the pre-concentrator.

23. The process of claim 22, further comprising:
heating the pre-concentrator to release chemicals or volatile organic compounds (VOCs) trapped therein; and
configuring the second three-way valve to form a flow path through with the chemicals or VOCs can flow from the pre-concentrator to one or both of the back-end pre-concentrator module and the gas analysis module.

24. The process of claim 23, further comprising directing chemicals or VOCs concentrated by the back-end pre-concentrator module into the gas analysis module.

25. The process of claim 22, further comprising providing a back-end pre-concentrator module comprising:
a pre-concentrator having an inlet and an outlet, the inlet being coupled to the second three-way valve and to the inlet of the gas chromatograph;
a fourth three-way valve coupled to the outlet of the pre-concentrator;
a trap coupled to the fourth three-way valve;
a second pump coupled to the fourth three-way valve;
a third three-way valve coupled to the second pump and coupled to a fluid connection between the outlet of the pre-concentrator and the fourth three-way valve.

26. A process comprising:
providing an apparatus including:
a front-end pre-concentrator module including an inlet, an outlet, and at least one valve to control flow through the inlet, the outlet, or both, the front-end pre-concentrator module including:
a pre-concentrator having an inlet and an outlet,
a first three-way valve coupled to the inlet of the pre-concentrator and a second three-way valve coupled to the outlet of the pre-concentrator,
a trap coupled to the first three way valve,
a third three-way valve coupled to the second three-way valve, and
a pump coupled to the third three-way valve;
a back-end pre-concentrator module including an inlet, an outlet, and at least one valve to control flow through the inlet, the outlet, or both; and
a gas analysis module having an inlet and an outlet and including a gas chromatograph having an inlet and an outlet, wherein the outlet of the front-end pre-concentrator and the outlet of the back-end pre-concentrator are coupled to the inlet of the gas analysis module;
configuring the at least one valve in the front-end pre-concentrator and the at least one valve in the back-end pre-concentrator to form a flow path to receive a gas sample through the front-end pre-concentrator, concentrate chemicals or volatile organic compounds carried by the gas and direct them to the gas analysis module, the back-end pre-concentrator module, or both; and
configuring the first and second three-way valves to form a flow path to receive a gas sample through the first three-way valve and concentrate chemicals or volatile organic compounds carried by the gas in the pre-concentrator.

27. The process of claim 26, further comprising:
heating the pre-concentrator to release chemicals or volatile organic compounds (VOCs) trapped therein; and
configuring the second three-way valve to form a flow path through with the chemicals or VOCs can flow from the pre-concentrator to one or both of the back-end pre-concentrator module and the gas analysis module.

28. The process of claim 27, further comprising directing chemicals or VOCs concentrated by the back-end pre-concentrator module into the gas analysis module.

29. The process of claim 26, further comprising providing a back-end pre-concentrator module comprising:

a pre-concentrator coupled to the third Y-splitter;
a fourth three-way valve coupled to the pump and to a vent; and
a fifth three-way valve coupled to the pre-concentrator, the third three-way valve and the fourth three-way valve.

30. A process comprising:
providing an apparatus including:
a front-end pre-concentrator module including an inlet, an outlet, and at least one valve to control flow through the inlet, the outlet, or both, the front-end pre-concentrator module including:
a pre-concentrator having an inlet and an outlet;
a first three-way valve coupled to the inlet of the pre-concentrator and a second three-way valve coupled to the outlet of the pre-concentrator;
a trap coupled to the first three way valve;
a third three-way valve coupled to the second three-way valve and to a first pump; and
an additional gas chromatograph having:
an inlet coupled to the second three-way valve, and
an outlet coupled to the inlet of the gas chromatograph, to the inlet of the back-end pre-concentrator, and to the third three-way valve;
a back-end pre-concentrator module including an inlet, an outlet, and at least one valve to control flow through the inlet, the outlet, or both; and
a gas analysis module having an inlet and an outlet and including a gas chromatograph having an inlet and an outlet, wherein the outlet of the front-end pre-concentrator and the outlet of the back-end pre-concentrator are coupled to the inlet of the gas analysis module;
configuring the at least one valve in the front-end pre-concentrator and the at least one valve in the back-end pre-concentrator to form a flow path to receive a gas sample through the front-end pre-concentrator, concentrate chemicals or volatile organic compounds carried by the gas and direct them to the gas analysis module, the back-end pre-concentrator module, or both.

31. The process of claim 30, further comprising:
heating the pre-concentrator to release chemicals or volatile organic compounds (VOCs) trapped therein; and
configuring the second three-way valve to form a flow path through with the chemicals or VOCs can flow from the pre-concentrator to one or both of the back-end pre-concentrator module and the gas analysis module.

32. The process of claim 31, further comprising directing chemicals or VOCs concentrated by the back-end pre-concentrator module into the gas analysis module.

33. The process of claim 30, further comprising providing a back-end pre-concentrator module comprising:
a pre-concentrator having an inlet and an outlet, the inlet being coupled to the inlet of the gas chromatograph and the outlet of the additional gas chromatograph;
a fourth three-way valve coupled to the outlet of the pre-concentrator;
a trap coupled to the fourth three-way valve;
a second pump coupled to the fourth three-way valve;
a fifth three-way valve coupled to the second pump and coupled to a fluid connection between the pre-concentrator and the fourth three-way valve.

* * * * *